United States Patent
Bond et al.

(10) Patent No.: US 6,696,546 B1
(45) Date of Patent: Feb. 24, 2004

(54) PEPTIDE THAT KILLS GROWING BUT NOT STATIONARY CELLS

(75) Inventors: Gareth Lane Bond, New York, NY (US); James L. Manley, Greenlawn, NY (US); Carol Prives, Greenlawn, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 120 days.

(21) Appl. No.: 09/707,263

(22) Filed: Nov. 6, 2000

(51) Int. Cl.[7] .................. C07K 14/46; C07K 19/00; C12N 4/02; A61K 38/08; A61K 39/17
(52) U.S. Cl. .................. 530/328; 530/325; 530/300; 530/514; 530/16; 530/13; 514/16; 514/13
(58) Field of Search .............. 514/12, 16, 13; 530/328, 325, 300; 424/94.5

(56) References Cited

FOREIGN PATENT DOCUMENTS

WO WO 93/11227 * 6/1993

OTHER PUBLICATIONS

Bolton, et al., 2000, Eur J Neurosci, 12(8):2847–55.*

Bond, G.L., Prives, C., and Manley, J.L. Poly(A) polymerase phosphorylation is dependent on novel interactions with cyclins. Mol. Cell. Biol. 20(14) : 5310–5320, Jul. 2000.

Chen, Y.–N. P., Sharma, S.K., Ramsey, T.M., Jiang, L., Martin, M.S., Baker, K., Adams, P.D., Bair, K.W, and Kaelin, W.G. Jr. Selective killing of transformed cells by cyclin/cyclin–dependen kinase 2 antagonists. Proc. Natl. Acad. Sci. 96: 4325–4329, Apr. 1999.

* cited by examiner

*Primary Examiner*—Mary E. Mosher
*Assistant Examiner*—Natalie Davis
(74) *Attorney, Agent, or Firm*—John P. White; Cooper & Dunham LLP

(57) ABSTRACT

The present invention provides purified and synthetic peptides comprising the amino acid sequences shown in SEQ ID NO: 1 and SEQ ID NO: 3. The invention also provides pharmaceutical compositions comprising the peptides and methods of killing dividing cells and treating abnormalities and tumors in a subject using the peptides.

4 Claims, 15 Drawing Sheets

PAP's CRM
Scrambled
cdk2/cyclin A
pRB ($^{32}$P)pRB
($^{32}$P)cyclin A

PAP's CRM
Scrambled
cdc2/cyclin B
pRB ($^{32}$P)pRB
($^{32}$P)cyclin B

Autoradiogram

Coomassie Blue Staining

Autoradiogram

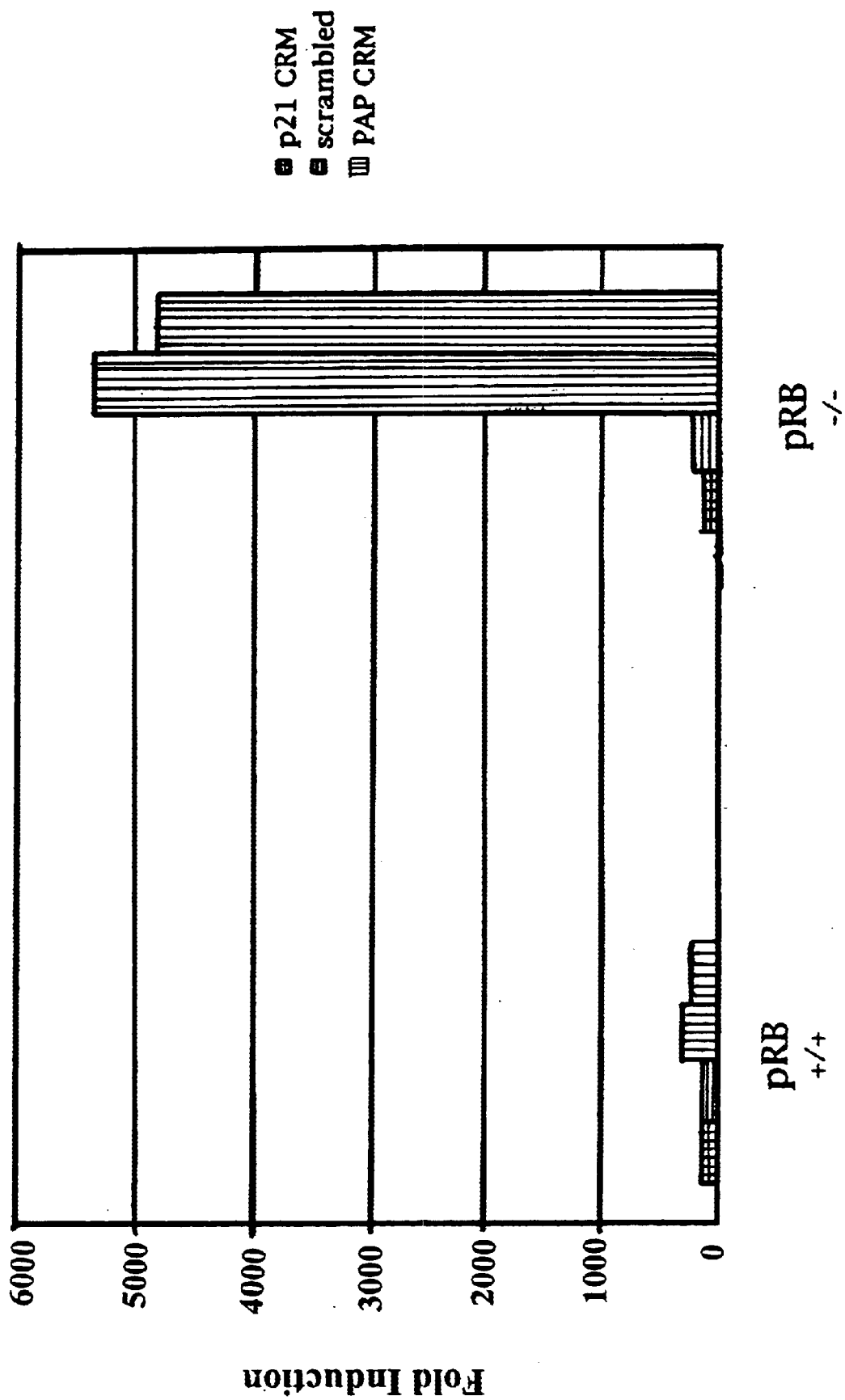

SEQUENCE LISTING

```
<160> NUMBER OF SEQ ID NOS: 17

<210> SEQ ID NO 1
<211> LENGTH: 8
<212> TYPE: PRT
<213> ORGANISM: Artificial Sequence
<220> FEATURE:
<223> OTHER INFORMATION: poly(A) polymerase cyclin recognition motif

<400> SEQUENCE: 1

Ser Lys Ile Arg Ile Leu Val Gly
1               5

<210> SEQ ID NO 2
<211> LENGTH: 16
<212> TYPE: PRT
<213> ORGANISM: Drosophilia Antennapedia

<400> SEQUENCE: 2

Arg Gln Ile Lys Ile Trp Phe Gln Asn Arg Arg Met Lys Trp Lys Lys
1               5                   10                  15

<210> SEQ ID NO 3
<211> LENGTH: 24
<212> TYPE: PRT
<213> ORGANISM: Artificial Sequence
<220> FEATURE:
<223> OTHER INFORMATION: poly(A) polymerase cyclin recognition motif
      fued to Drosohilia Antennapedia homeodomain residues

<400> SEQUENCE: 3

Arg Gln Ile Lys Ile Trp Phe Gln Asn Arg Arg Met Lys Trp Lys Lys
1               5                   10                  15
Ser Lys Ile Arg Ile Leu Val Gly
            20

<210> SEQ ID NO 4
<211> LENGTH: 8
<212> TYPE: PRT
<213> ORGANISM: Artificial Sequence
<220> FEATURE:
<223> OTHER INFORMATION: scrambled sequence

<400> SEQUENCE: 4

Leu Arg Ser Gly Ile Lys Val Ile
1               5

<210> SEQ ID NO 5
<211> LENGTH: 8
```

```
<212> TYPE: PRT
<213> ORGANISM: Homo Sapiens

<400> SEQUENCE: 5

Lys Ala Cys Arg Arg Leu Phe Gly
1               5

<210> SEQ ID NO 6
<211> LENGTH: 8
<212> TYPE: PRT
<213> ORGANISM: Homo Sapiens

<400> SEQUENCE: 6

Ser Ala Cys Arg Asn Leu Phe Gly
1               5

<210> SEQ ID NO 7
<211> LENGTH: 8
<212> TYPE: PRT
<213> ORGANISM: Homo Sapiens

<400> SEQUENCE: 7

Ser Ala Cys Arg Ser Leu Phe Gly
1               5

<210> SEQ ID NO 8
<211> LENGTH: 8
<212> TYPE: PRT
<213> ORGANISM: Homo Sapiens

<400> SEQUENCE: 8

Lys Ala Cys Arg Arg Leu Phe Gly
1               5

<210> SEQ ID NO 9
<211> LENGTH: 8
<212> TYPE: PRT
<213> ORGANISM: Homo Sapiens

<400> SEQUENCE: 9

His Ser Lys Arg Arg Leu Ile Phe
1               5

<210> SEQ ID NO 10
<211> LENGTH: 8
<212> TYPE: PRT
<213> ORGANISM: Homo Sapiens

<400> SEQUENCE: 10

Ser Ala Lys Arg Arg Leu Phe Gly
1               5

<210> SEQ ID NO 11
<211> LENGTH: 8
<212> TYPE: PRT
<213> ORGANISM: Homo Sapiens

<400> SEQUENCE: 11

Thr Thr Arg Arg Arg Leu Phe Val
1               5

<210> SEQ ID NO 12
<211> LENGTH: 8
<212> TYPE: PRT
<213> ORGANISM: Homo Sapiens
```

```
<400> SEQUENCE: 12

Pro Val Lys Arg Arg Leu Asp Leu
1               5

<210> SEQ ID NO 13
<211> LENGTH: 8
<212> TYPE: PRT
<213> ORGANISM: Homo Sapiens

<400> SEQUENCE: 13

Pro Ala Pro Arg Arg Leu Leu Phe
1               5

<210> SEQ ID NO 14
<211> LENGTH: 8
<212> TYPE: PRT
<213> ORGANISM: Homo Sapiens

<400> SEQUENCE: 14

Lys Ala Lys Arg Arg Leu Phe Thr
1               5

<210> SEQ ID NO 15
<211> LENGTH: 8
<212> TYPE: PRT
<213> ORGANISM: Homo Sapiens

<400> SEQUENCE: 15

Lys Pro Leu Lys Lys Leu Arg Phe
1               5

<210> SEQ ID NO 16
<211> LENGTH: 8
<212> TYPE: PRT
<213> ORGANISM: Homo Sapiens

<400> SEQUENCE: 16

Pro Thr Leu Lys Thr Leu Gln Val
1               5

<210> SEQ ID NO 17
<211> LENGTH: 8
<212> TYPE: PRT
<213> ORGANISM: Homo Sapiens

<400> SEQUENCE: 17

Ser Ala Lys Arg Arg Leu Phe Gly
1               5
```

PEPTIDE THAT KILLS GROWING BUT NOT STATIONARY CELLS

The invention disclosed herein was made with Government support under grant numbers R01 GM 28983, CA 58316 and CA 77742 from the National Institutes of Health, U.S. Department of Health and Human Services. Accordingly, the U.S. Government has certain rights in this invention.

BACKGROUND OF THE INVENTION

Throughout this application, various publications are referenced in parentheses by number. Full citations for these references may be found at the end of the specification immediately preceding the claims. The disclosures of these publications in their entireties are hereby incorporated by reference into this application to more fully describe the state of the art to which this invention pertains.

The in-depth study of the molecular mechanisms behind cancer has enabled the design of small molecules that specifically target cancer cells and kill them. This will hopefully reduce host toxicity, but still be lethal to cancer cells. One avenue of intervention for these molecules is manipulating the cell cycle.

Cyclin-dependent kinases (cdk) are significant players in regulating the entry into, and progression of, the eukaryotic cell cycle (reviewed in 1, 2). Notably, selective killing of transformed cells by cyclin/cdk 2 antagonists has already been shown (30).

An important cdk substrate involved in gene expression is poly adenylate polymerase (PAP). This enzyme catalyzes the polyadenylation of the 3' poly(A) tail found in almost all eukaryotic messenger ribonucleic acids (mRNA). The polyadenylation reaction affects, and is affected by, steps in mRNA synthesis, and so can constitute a significant point of regulation, utilized by the cell, to control gene expression (reviewed in 3). A growing body of evidence suggests this to be the case in early development (4), in cell differentiation (5, 6) and in M-phase (mitotic phase) of the cell cycle. Regulation of polyadenylation via control of PAP activity, including the effect of phosphorylation of PAP on its activity in vitro and in vivo assays has been shown (7, 8, 9).

All known vertebrate PAPs contain a C-terminal serine- and threonine-rich domain with multiple cyclin-dependent kinase sites. These sites are phosphorylated in vitro and in vivo by cyclin B/p34cdc2 (10). Cyclin B/p34cdc2 is a member of the cdk family, with all members being heterodimers containing a kinase subunit (the cdk) and a regulatory subunit (the cyclin). Cyclin binding to the catalytic subunit imparts upon the cdk much of its substrate specificity (11, 12, 13, 14, 15). Some cdk substrates contain a sequence, the cyclin recognition motif (CRM), which is thought responsible for the interaction of cdk substrates with the cyclin. This sequence, the CRM, is now known to be shared by inhibitors (p21, p27 and p57) and substrates (e.g., E2F-1, p130, p107, and pRB) alike (16, 17, 18, 19, 20, 21, 22, 23, 24, 25, 26).

The present application discloses that PAP binds directly to both G1- and G2-type cyclins, and that cyclin binding is mediated by a stretch of amino acids with similarity to the consensus CRM. Furthermore, the present application discloses an 8-mer peptide, spanning PAP's CRM, which regulates phosphorylation of CRM containing proteins such as the retinoblastoma gene product (pRB) by cdks. Notably, low concentrations of the 8-mer peptide inhibit cdk-mediated pRB phosphorylation.

The present application discloses that this 8-mer peptide, spanning PAP's CRM, is lethal to growing cells. If the cell is dividing, the peptide kills the cell. However, if the cell is stationary, the peptide actively protects the cell from death. CRM peptides previously reported to kill cells (30) are much more limited in effect and only kill some cancer cells, leaving other immortalized cells untouched. In contrast, the membrane permeable PAP CRM peptide sequence disclosed in this application (SEQ ID NO: 3) kills all dividing cells tested thus far, including cells the prior art cannot.

More importantly, the peptide disclosed here is much more effective in killing cells with an inactive pRB than it is in killing normal growing cells (up to 50 times more). The peptide is thus more efficient at killing the dividing cells of the type found in neoplasias (up to 90% of neoplasias are thought to have an inactive pRB) than other dividing cells in the body, such as those in the gut. Potentially, the peptide will specifically target cancer cells and kill them whilst showing reduced host toxicity as compared to other treatments.

SUMMARY OF THE INVENTION

The present invention provides a peptide comprising the amino acid sequence shown in SEQ ID NO: 1, wherein the peptide is a purified peptide or a synthetic peptide. The present application also provides a peptide comprising the amino acid sequence shown in SEQ ID NO: 3, wherein the peptide is a purified peptide or a synthetic peptide.

The invention provides a method of killing a dividing cell, which comprises applying to the cell an amount of any of the peptides described herein effective to kill the cell.

The invention provides a method of treating a tumor in a subject, which comprises administering to the subject an amount of any of the peptides described herein effective to treat the tumor.

The invention provides a method of treating an abnormality in a subject, which comprises administering to the subject an amount of any of the peptides described herein effective to alleviate the abnormality, wherein the abnormality is alleviated by killing dividing cells.

The invention provides a pharmaceutical composition comprising any of the peptides described herein and a pharmaceutically acceptable carrier.

The invention provides the use of any of the peptides described herein for the preparation of a pharmaceutical composition for treating an abnormality, wherein the abnormality is alleviated by killing dividing cells.

The invention provides a method of protecting a non-dividing cell from cell death which comprises applying to the cell an amount of any of the peptides described herein effective to protect the cell.

Figure 1A:
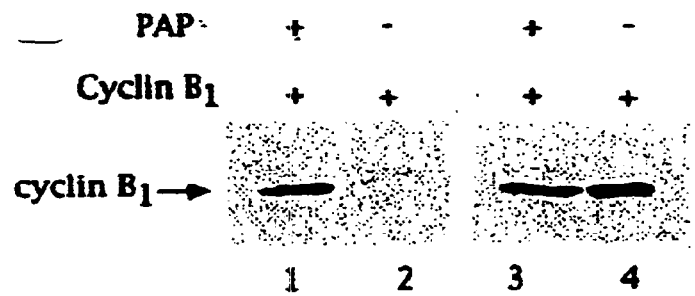
FIG. 1. PAP binds cyclin $B_1$ in vivo and in vitro.

(A) PAP associates with cyclin $B_1$ in vivo. Coimmunoprecipitation and Western blot analysis of sf9 insect cell extracts made from cells infected with recombinant baculoviruses expressing either PAP and cyclin $B_1$, or cyclin $B_1$ alone. Lysates were immunoprecipitated with a polyclonal antibody raised against PAP. The immunoprecipitates (lanes 1 and 2), and 10% of the cell extracts used (lanes 3 and 4), were subjected to SDS-PAGE and subsequent Western blot analysis using a monoclonal antibody against human cyclin $B_1$. The position of cyclin $B_1$ is indicated.

(B) PAP binds cyclin $B_1$/cdc2 directly. Purified PAP II (1 μg; strips 1 and 2), purified p53 (1 μg; strip 3), and bacterial whole-cell extract expressing human cyclin $B_1$ (strip 4) were first immobilized on nitrocellulose. Following renaturation by serial dilution with guanidine-HCl, strips 1, 3 and 4 were incubated with purified cyclin $B_1$/cdc2 (100 ng). After washing, cyclin $B_1$ was detected by immuno-reactivity to the anti-cyclin $B_1$ antibody. An arrow on the left indicates the position of PAP II. An arrow on the right indicates the position of cyclin $B_1$.

FIG. 2. PAP binds cyclin $B_1$ via residues N-terminal of its Ser/Thr-rich regulatory region.

GST-Cyclin $B_1$ "pull-down" assays were performed using purified GST or GST fusion proteins bound to a glutathione matrix and in vitro translated $^{35}$S labeled PAPs (2 μls). (A) Autoradiogram of the elutes of either GST-Cyclin $B_1$ (lane 1) or GST (lane 2) glutathione matrices and 10% of the input PAP I (lane 3). An arrow on the left indicates the position of PAP I.

(B) A schematic representation of PAP species used in the assay depicted in panel D, and summary of results. The black region indicates the Ser/Thr-rich region and the white bars indicate the sites for cdk phosphorylation. The bipartite nuclear localization signal sequences are boxed in gray. A plus indicates observed binding, two pluses indicate strongest binding, and a minus indicates no binding observed.

(C) Autoradiogram of $^{35}$S labeled PAP's bound to either GST-Cyclin B1 (lanes 1,3,5, and 7) or GST (lanes 2,4,6, and 8). Lanes 9–12 are 10% of the input PAP's. The roman numerals indicate the PAP species used as graphically represented in panel C.

Figure 3:
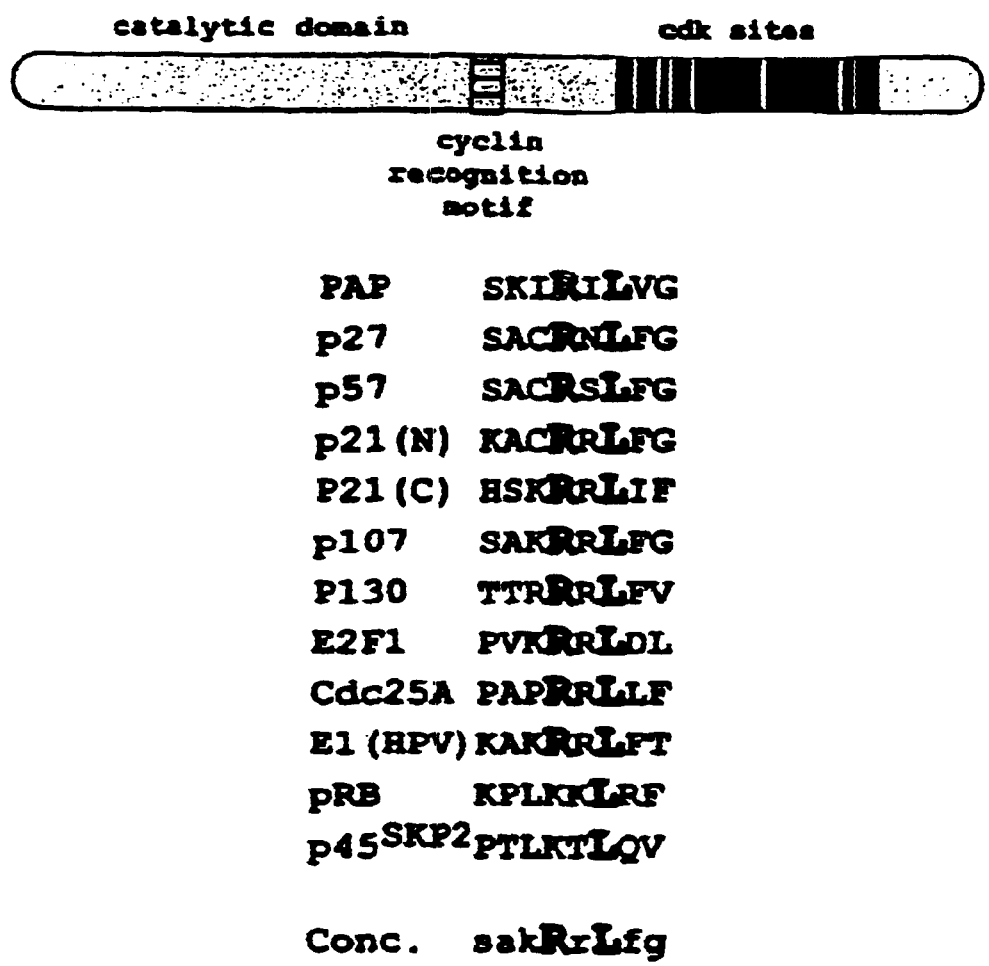

FIG. 3. PAP contains a Cyclin Recognition Motif (CRM).

A schematic representation of PAP is shown at the top. The cyclin recognition motif is boxed and striped and the Ser/Thr-rich regulatory region is boxed in black, with white bars representing the cdk sites and gray bars representing the NLS's. Below is an alignment of CRMs with the highly conserved arginine and leucine residues highlighted (PAP, SEQ ID NO:1; p27, SEQ ID NO:6; p57, SEQ ID NO:7; p21(N), SEQ ID NO:8; p21(C), SEQ ID NO:9; p107, SEQ ID NO:10; P130, SEQ ID NO:11; E2F1, SEQ ID NO:12; Cdc25A, SEQ ID NO:13; E1(HPV), SEQ ID NO:14; pRB, SEQ ID NO:15; p45$^{SKP2}$, SEQ ID NO:16; and Conc., SEQ ID NO:17). The CRM consensus contains the nearly invariant arginine and leucine residues and, in lower case, the residues found most frequently at the other positions.

FIG. 4. PAP contains a functional CRM.

Inhibition of cdk phosphorylation of pRB by an 8-mer PAP-derived peptide. (A) Purified pRB and cyclin A/cdk2 were incubated under kinase conditions in the presence of γ-$^{32}$P ATP and two concentrations (9 μM and 18 μM) of either an 8-mer PAP CRM-derived peptide (SKIRILVG, SEQ ID NO: 1) (lanes 2 and 3), an 8-mer peptide of scrambled sequence (LRSGIKVI, SEQ ID NO: 4)(lanes 4 and 5) or no peptide (lane 1). Phosphorylated proteins were resolved by SDS-PAGE and detected by autoradiography. Arrows on the left indicates the positions of pRB and cyclin A. (B) Purified pRB and cyclin $B_1$/cdc2 were incubated under kinase conditions in the presence of γ-$^{32}$P ATP and the 8-mer PAP CRM-derived peptide (SEQ ID NO: 1) (18 μM) (lane 2), the 8-mer peptide of scrambled sequence (SEQ ID NO: 4) (18 μM) (lane 3) or no peptide (lane 1). Arrows on the left indicates the positions of pRB and cyclin $B_1$.

Figure 5A:
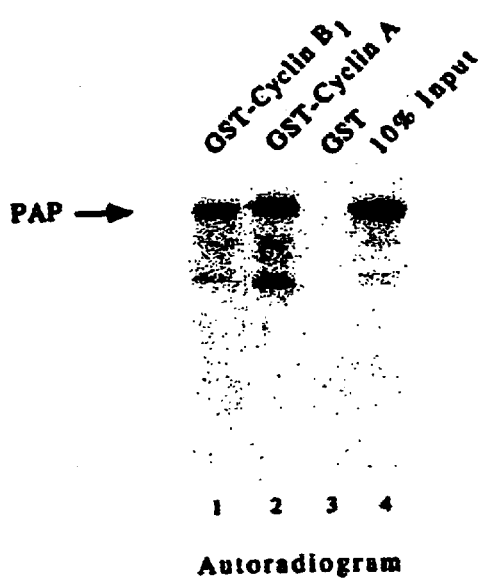

FIG. 5. PAP binds cyclin A and is phosphorylated by cyclin A/cdk 2.

(A) Autoradiogram of in vitro translated $^{35}$S labeled PAP bound to GST-Cyclin $B_1$ (lane 1), GST-Cyclin A (lane 2), or GST (lane 3) glutathione matrices and 10% of the input PAP I (lane 4). An arrow on the left indicates the position of PAP. (B) Coomasie blue stained SDS-PAGE of purified GST-Cyclin A (lane 2) and GST-Cyclin $B_1$ (lane 3) fusion proteins used in the binding reactions. (C) Autoradiogram of phosphorylated PAP after incubation with cyclin A/cdk2. Purified PAP and cyclin A/cdk2 were incubated under kinase conditions in the presence of γ-$^{32}$P ATP (lane 1). Specific inhibitors of cdks, olomoucine (14 μM and 70 μM) (lanes 2 and 3) and roscovitine (7 μM and 14 μM) (lanes 4 and 5), were added to establish the specificity of the reaction. Phosphorylated proteins were resolved by SDS-PAGE and detected by autoradiography. An arrow on the left indicates the position of PAP.

FIG. 6. PAP's CRM (SEQ ID NO: 1) both activates and represses PAP binding to cyclin $B_1$.

The effect of the 8-mer PAP CRM-derived peptide (SEQ ID NO: 1) in GST-Cyclin-PAP "pull-down" assays was tested. (A) GST-Cyclin $B_1$ glutathione matrices were incubated with in vitro translated $^{35}$S labeled PAP (1 μl) in the presence (or absence; lane 1) of increasing amounts of PAP's CRM peptide (SEQ ID NO: 1) (9, 18, 36 and 72 μM; lanes 2, 3, 4 and 5). Samples were washed and bound proteins were analyzed by 10% SDS-PAGE and autoradiography. An arrow on the left indicates the position of PAP. 100% of the $^{35}$S labeled PAP used in each reaction is found in lane 6.

(B) Concentration dependence of the PAP CRM stimulatory effect. Lower concentrations of PAP's CRM peptide (SEQ ID NO: 1) were used in binding assays similar to those in (A) (2.25, 4.5, 9 and 18 μM; lanes 2, 3, 4 and 5), as well as identical amounts of the 8-mer peptide of scrambled sequence (SEQ ID NO: 4) (lanes 6, 7, 8 and 9).

(C) CRM enhancement of PAP-Cyclin $B_1$ binding reflects a direct interaction. GST-Cyclin $B_1$ glutathione matrices were incubated with purified bacterial PAP in the presence of increasing amounts (2, 8.6 and 17 μM) of either PAP's CRM (SEQ ID NO:1) (lanes 3, 4 and 5), p21's CRM (SEQ ID NO: 5) (lanes 6, 7, and 8) or no peptide (lane 1). Samples were subjected to SDS-PAGE and subsequent Western blot analysis using a PAP polyclonal antibody.

(D) PAP's CRM (SEQ ID NO: 1) can enhance cyclin-cdk association. GST-Cyclin $D_1$ glutathione matrices were incubated with purified HA-tagged cdk2 in the presence of increasing amounts (9 μM and 18 μM) of either PAP's CRM (lanes 3 and 4), a control peptide (SEQ ID NO: 4) (lanes 5 and 6) or no peptide (lane 2). The presence of cdk2 in the eluates was detected by Western blot analysis using a monoclonal antibody against the HA-epitope.

Figure 7:
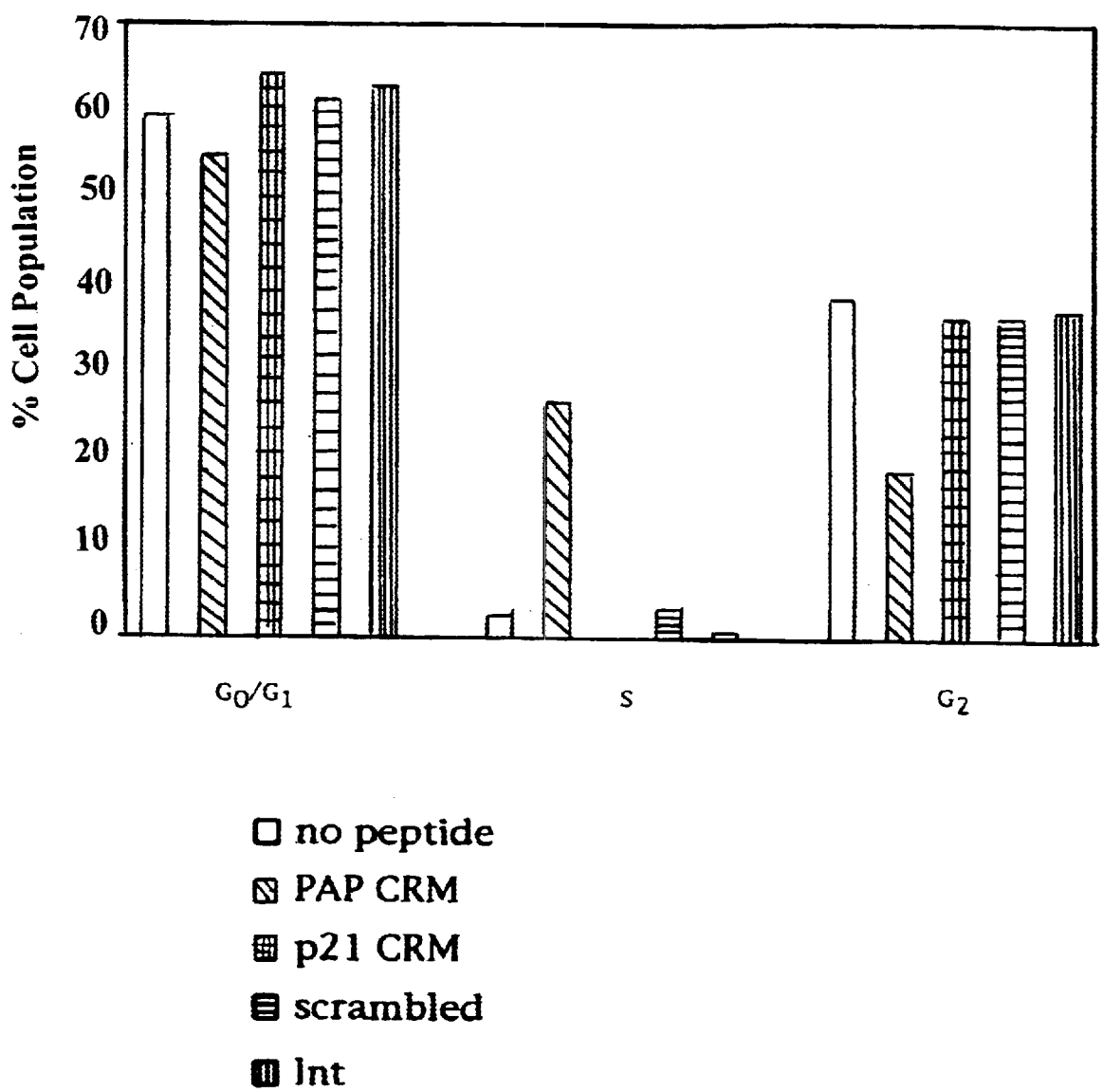

FIG. 7. PAP's CRM (SEQ ID NO: 3) stimulates cell proliferation in resting human cells (HaTCaT cells).

A graphical representation of DNA content of cells as collected by propidium iodide staining and subsequent FACS analysis. $G_0/G_1$, S, and $G_2M$ phases are depicted of cells either treated or not treated with cell permeable peptides. The percentage of untreated cell in a given phase are in white, PAP's CRM in (SEQ ID NO: 3) black, p21's in gray (SEQ ID NO: 5), scrambled in horizontal stripes (SEQ ID NO: 4), internalization sequence alone in vertical stripes (SEQ ID NO: 2).

Figure 8A:
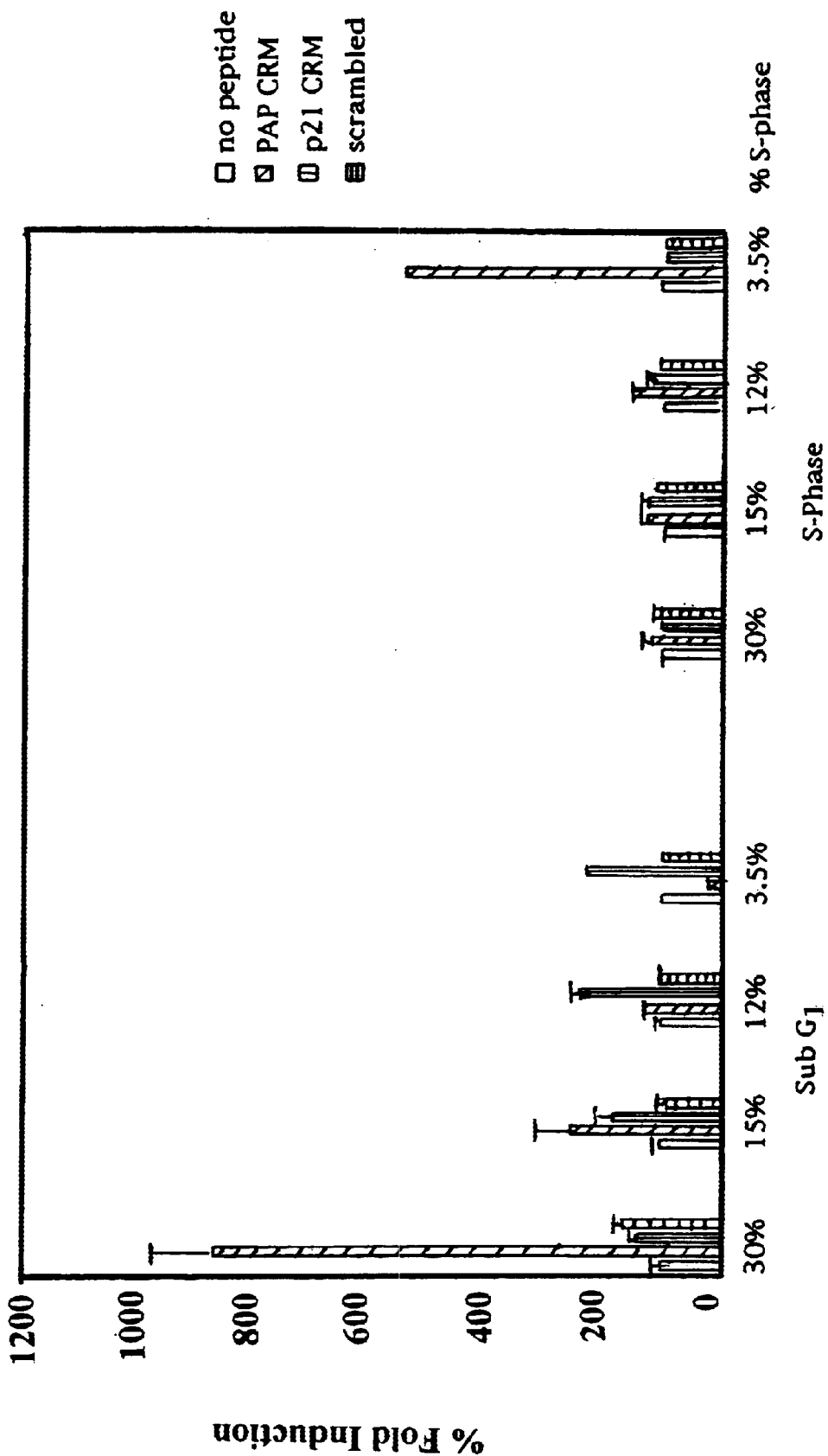

FIG. 8. PAP's CRM (SEQ ID NO: 3) kills growing cells, but not stationary cells.

(A) PAP's CRM (SEQ ID NO: 3) kills growing HaTCats, but stimulates S-phase entry of stationary HaTCats. The bar graph depicts the fold induction over non-treated cells of sub-$G_1$ DNA content and S-phase DNA content of four different populations of cells. The percentage of cells found S-phase of each population is noted below the bar graph. Sub-$G_1$ DNA content and S-phase DNA content are depicted of cells either treated or not treated with cell permeable peptides. The percentages of untreated cell in a given phase are in white, PAP's CRM (SEQ ID NO: 3) in black, p21's in gray (SEQ ID NO: 5), and scrambled in stripes (SEQ ID NO: 4).

(B) PAP's CRM kills growing Wi38s, but not stationary Wi38s. The bar graph depicts the fold induction over non-treated cells of sub-G1 DNA content. Experiments with three different populations of cells, with varying percentages of cells found in S-phase (as indicated in the percentages below the bar graph) are represented. The percentages of untreated cell are in white, PAP's CRM (SEQ ID NO: 3) in black, and scrambled (SEQ ID NO: 4) in stripes.

Figure 9:
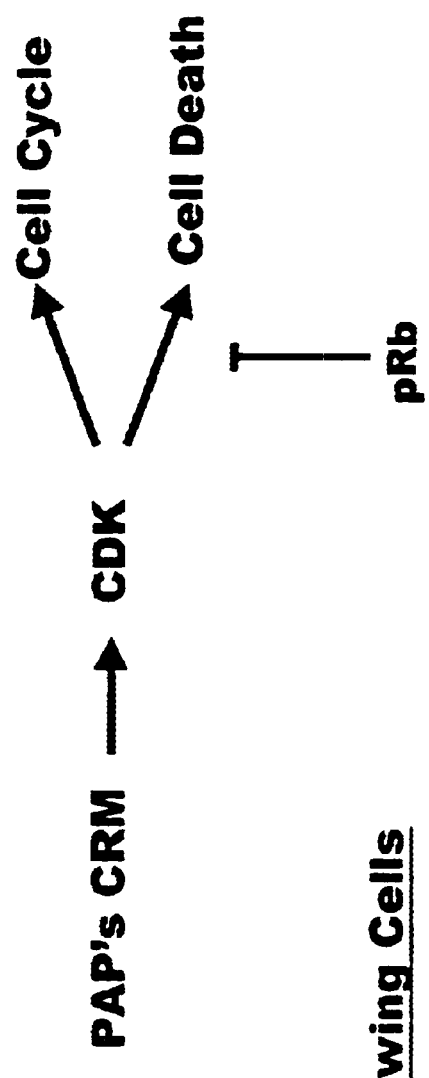
Figure 9:
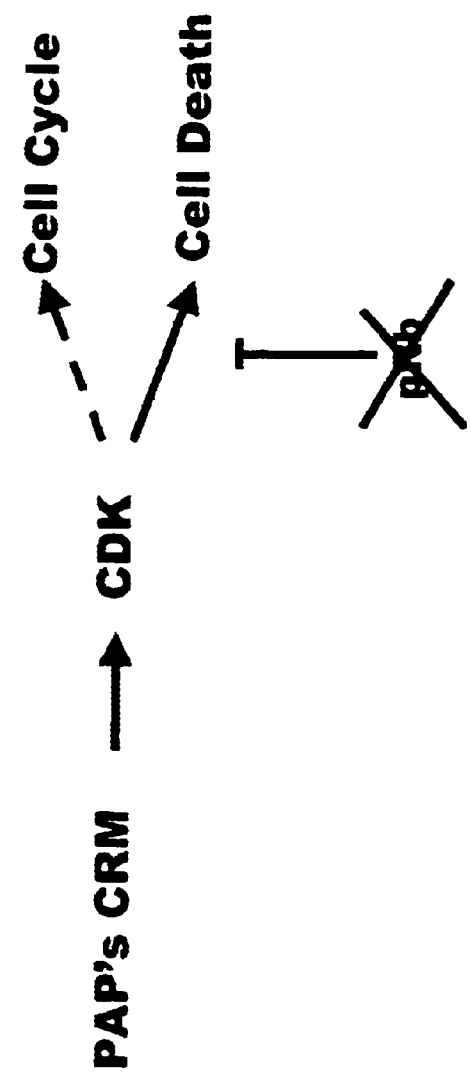

FIG. 9. PAP's CRM (SEQ ID NO: 3) kills growing cells, but resting cells are stimulated to proliferate.

A model to explaining the two different reactions to the same stimulus. PAP's CRM regulates cdk activity, which drives the cell into either the cell cycle or cell death. In resting cells, pRB is active and able to protect the cell from cell death and therefore allows stimulation of proliferation. In growing, cycling cells, pRB is inactivated by hyperphosphorylation, and can no longer inhibit cell death caused by PAP's CRM (SEQ ID NO: 3) and therefore cells can only die.

Figure 10A:
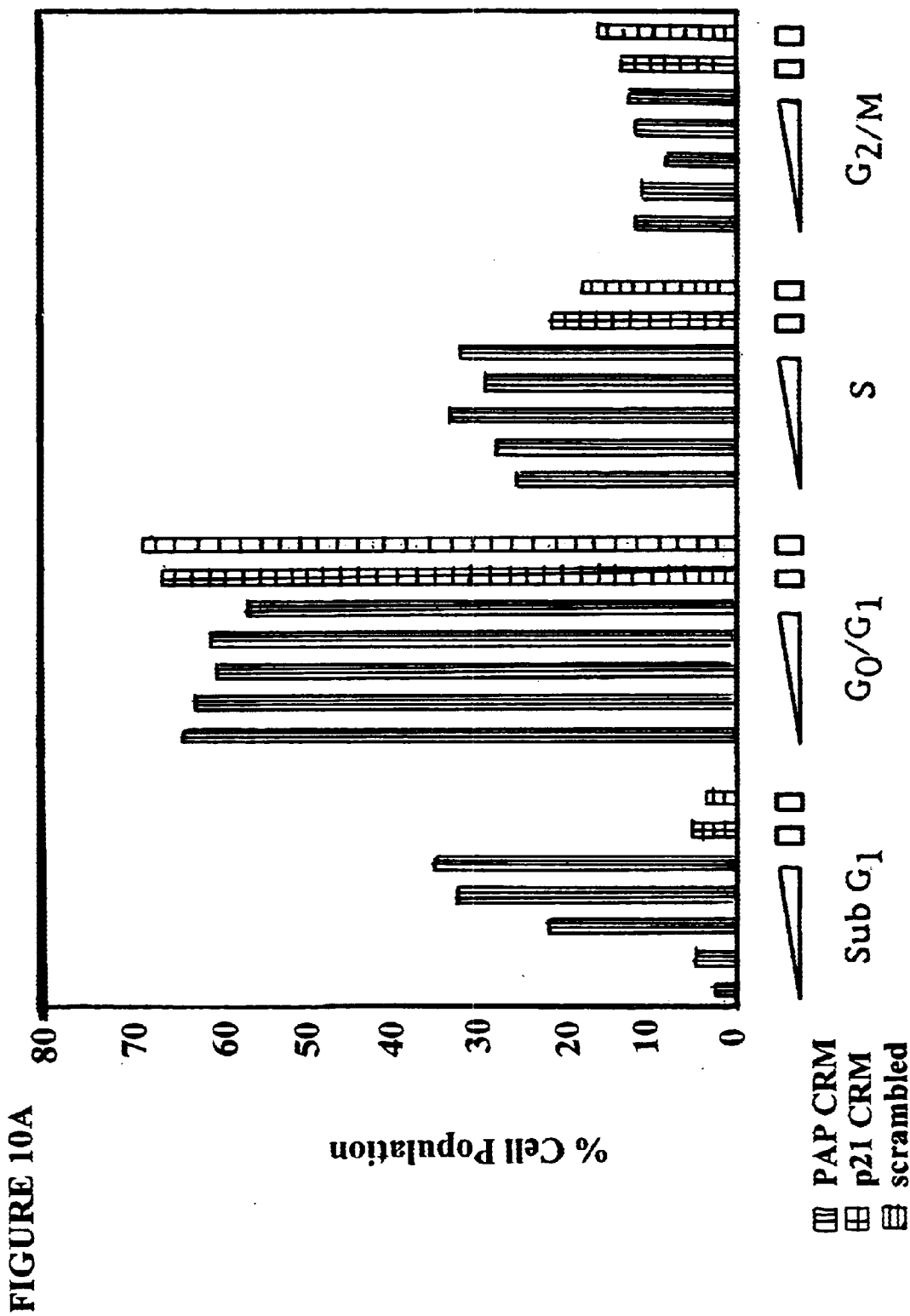
Figure 10B:
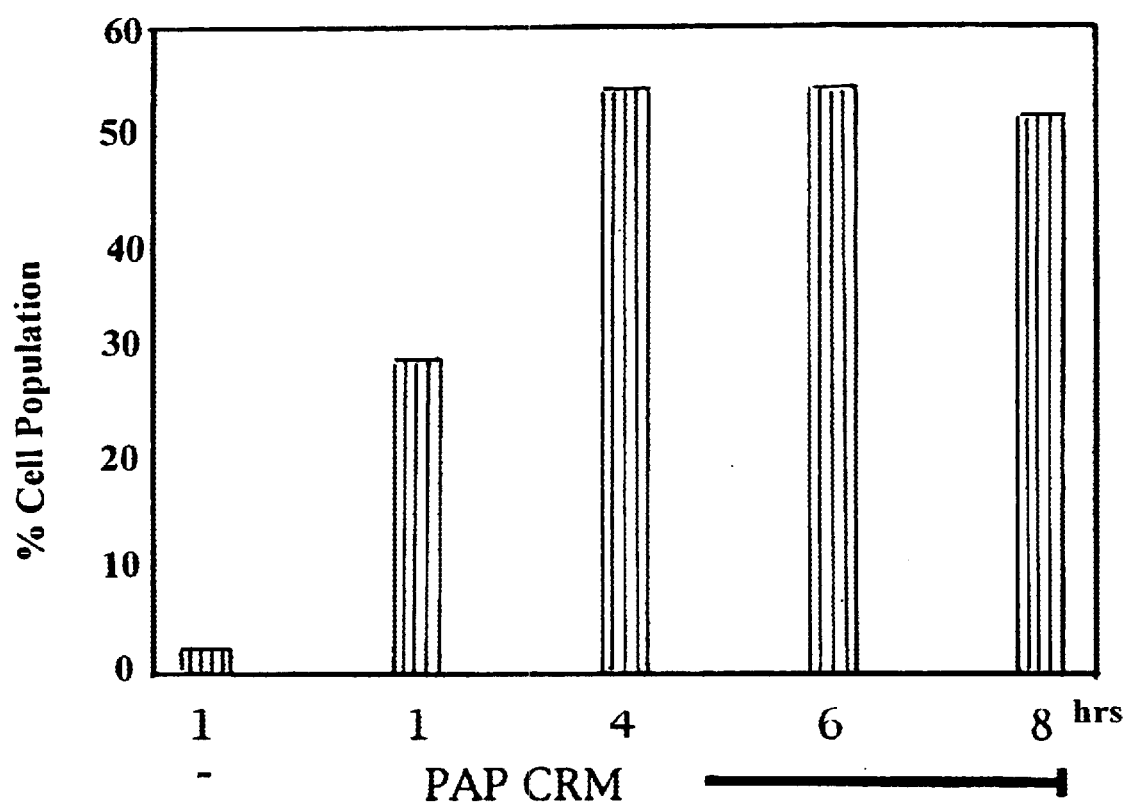
Figure 10C:
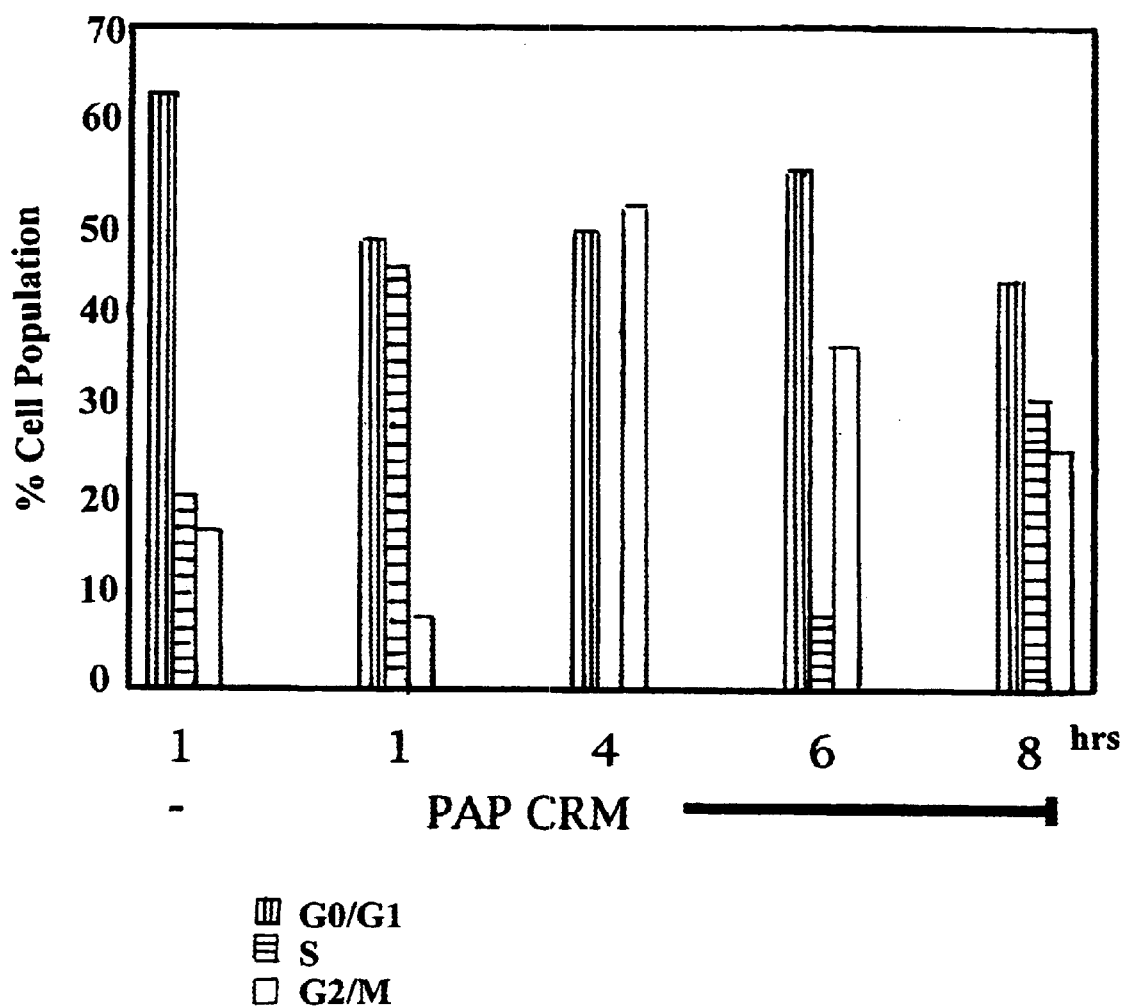

FIG. 10. PAP's CRM (SEQ ID NO: 3) stimulates both death and cell cycle progression in growing MEFs.

(A) PAP's CRM stimulates both the percentage of cells with sub-$G_1$ DNA content and S-phase DNA content in a dose dependent manner. DNA content as measured by FACS analysis is graphically represented. Sub-$G_1$, $G_0/G_1$, S, and $G_2/M$ DNA contents of cells are depicted after treatment with either varying concentrations of PAP's CRM (SEQ ID NO: 3) (in black; 1.87, 3.75, 7.5, 15, and 30 $\mu$M), p21's CRM (SEQ ID NO: 5) (in gray; 30 $\mu$M), or scrambled sequence (SEQ ID NO: 4) (in stripes; 30 $\mu$M)

(B) PAP's CRM stimulates cell death over time. The percentage of cells with a sub-G1 DNA content with or without treatment with 30 $\mu$M of PAP's CRM (SEQ ID NO: 3) for varying lengths of time is shown.

(C) The percents of cells with $G_0/G_1$ (in black), S (in gray), and $G_2/M$ (in white) DNA contents of the same population of cells in (B) are depicted.

Figure 11B:
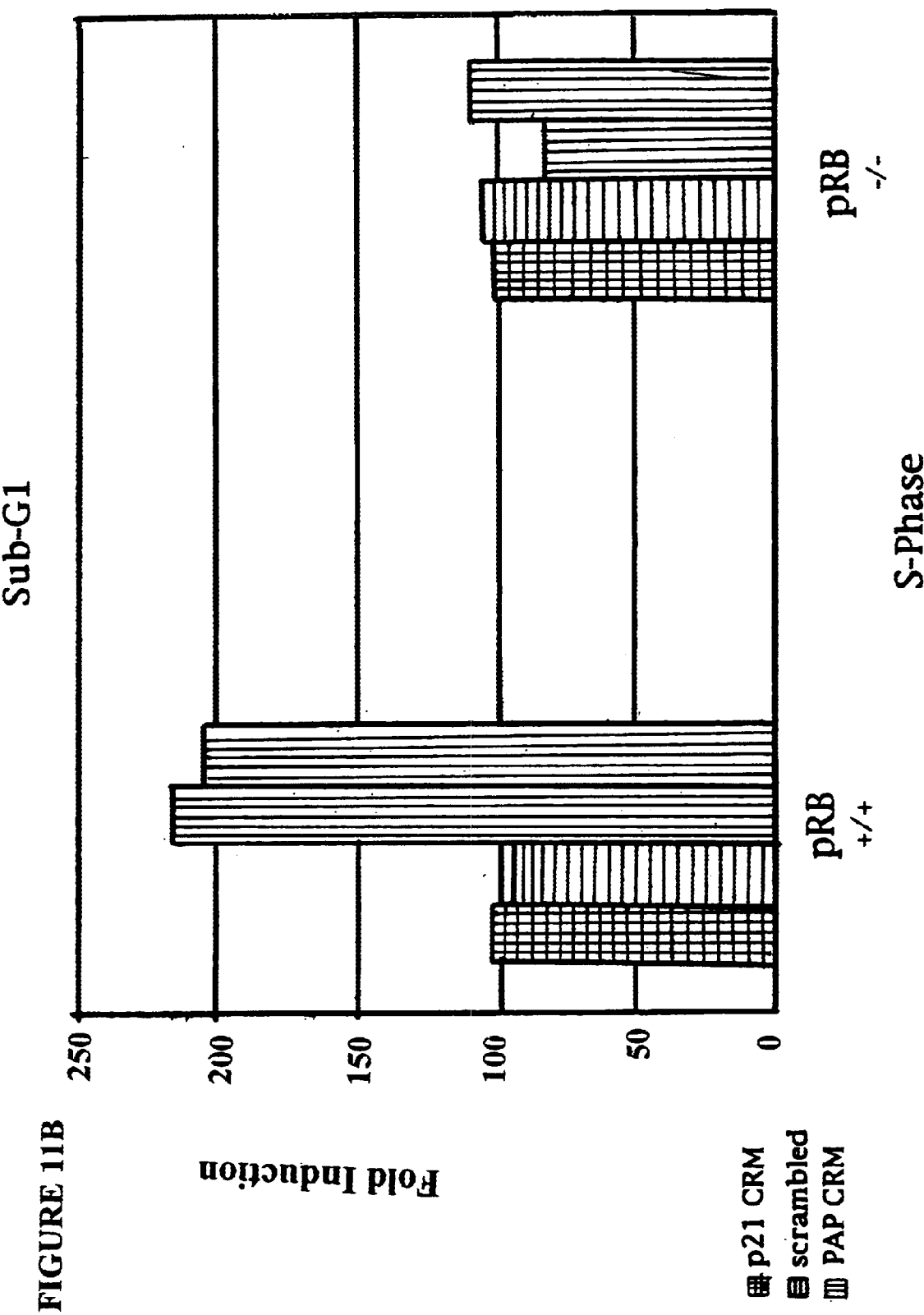

FIG. 11. PAP's CPM (SEQ ID NO: 3) stimulates only death in pRB knock out MEFs.

(A) A graphical representation of the fold induction of sub-G1 DNA content in cells with or without pRB, as indicated below the graph. Cell were treated with either p21's CRM (SEQ ID NO: 5) (in gray), scrambled (SEQ ID NO: 4) (in stripes), or PAP's CRM (SEQ ID NO: 3) (in black). (B) A graphical representation of the fold induction of S-phase DNA content in the same cells.

DETAILED DESCRIPTION OF THE INVENTION

The following definitions are presented as an aid in understanding this invention:
8-mer—8 amino acid peptide,
cdk—cyclin-dependent kinase,
CRM—cyclin recognition motif,
EDTA—ethylenediaminetetraacetic acid
FACS—fluorescence-activated cell sorter,
$G_0$ phase—exited from cell cycle,
$G_1$ phase—first gap of cell cycle,
$G_2$ phase—second gap of cell cycle,
growing cell—a dividing cell,
GST—glutathione-s-transferase,
HatCat—a human karitinocyte cell line,
M Phase—mitotic phase of cell cycle,
MEF—mouse embryo fibroblast,
p21—a cdk inhibitor,
p34cdc2—a specific cdk,
PAP—poly(A) polymerase,
PAP's CRM—PAP's cyclin recognition motif, referred to as SEQ ID NO: 1 if the 8-mer or SEQ ID NO: 3 if the membrane permeable version,
PBS—phosphate buffered saline,
pRB—retinoblastoma protein,
resting cell—a non-dividing cell,
S phase—DNA synthesis phase of cell cycle,
SDS PAGE—sodium dodecyl sulfate polyacrylamide electrophoresis
stationary cell—a non-dividing cell,
Wi38—an immortalized human cell line.

The following standard abbreviations are used for amino acids:

| 3-character abbreviation | Amino Acid | 1-character abbreviation |
|---|---|---|
| Ala | Alanine | A |
| Arg | Arginine | R |
| Asn | Asparagine | N |
| Asp | Aspartic Acid | D |
| Cys | Cysteine | C |
| Gln | Glutamine | Q |
| Glu | Glutamic Acid | E |
| Gly | Glycine | G |
| His | Histidine | H |
| Ile | Isoleucine | I |
| Leu | Leucine | L |
| Lys | Lysine | K |
| Met | Methionine | M |
| Phe | Phenylalanine | F |
| Pro | Proline | P |
| Ser | Serine | S |
| Thr | Threonine | T |
| Trp | Tryptophane | W |
| Tyr | Tyrosine | Y |
| Val | Valine | V |
| Asx | Asparagine/ Aspartic Acid | B |
| Glx | Glutamine/ Glutamic Acid | Z |
| * * * | (End) | * |
| Xxx | Unidentified | X |

Having due regard to the preceding definitions, the present invention provides a peptide comprising the amino acid sequence shown in SEQ ID NO: 1, wherein the peptide is a purified peptide or a synthetic peptide. The present application also provides a peptide comprising the amino acid sequence shown in SEQ ID NO: 3, wherein the peptide is a purified peptide or a synthetic peptide. In different embodiments of the invention, any of the peptides described herein are permeable to a cell membrane.

The invention provides a method of killing a dividing cell, which comprises applying to the cell an amount of any of the peptides described herein effective to kill the cell. In one embodiment, the cell contains a retinoblastoma gene product which is inactive. In one embodiment, the peptide regulates cyclin-dependent kinase activity. In one embodiment, the cell is a mammalian cell. In one embodiment, the mammalian cell is a human cell. In one embodiment, the cell is a tumor cell.

The invention provides a method of treating a tumor in a subject, which comprises administering to the subject an amount of any of the peptides described herein effective to treat the tumor.

The invention provides a method of treating an abnormality in a subject, which comprises administering to the subject an amount of any of the peptides described herein effective to alleviate the abnormality, wherein the abnormality is alleviated by killing dividing cells. In one embodiment, the abnormality is a tumor.

The invention provides a pharmaceutical composition comprising any of the peptides described herein and a pharmaceutically acceptable carrier. In one embodiment, the peptide and the carrier are capable of passing through a cell membrane.

The invention provides the use of any of the peptides described herein for the preparation of a pharmaceutical composition for treating an abnormality, wherein the abnormality is alleviated by killing dividing cells. In one embodiment, the abnormality is a tumor.

The invention provides a method of protecting a non-dividing cell from cell death which comprises applying to the cell an amount of any of the peptides described herein effective to protect the cell. In one embodiment, the cell is a mammalian cell. In one embodiment, the mammalian cell is a human cell.

In the subject invention, a "pharmaceutically effective amount" is any amount of a compound which, when administered to a subject suffering from a disease against which the compound is effective, causes reduction, remission, or regression of the disease. Furthermore, as used herein, the phrase "pharmaceutically acceptable carrier" means any of the standard pharmaceutically acceptable carriers. Examples include, but are not limited to, phosphate buffered saline, physiological saline, water, and emulsions, such as oil/water emulsions.

The following Experimental Details are set forth to aid in an understanding of the invention, and are not intended, and should not be construed, to limit in any way the invention set forth in the claims which follow thereafter.

EXPERIMENTAL DETAILS

Poly (A) Polymerase Interacts Both in vivo and in vitro With Cyclin $B_1$

PAP is regulated by cyclin B/p34cdc2 phosphorylation, which involves multiple cdk consensus (S/TPXK/R) and non-consensus (S/TP) sites, and the inhibition of its catalytic activity upon hyperphosphorylation (7, 10). Given that some cdk substrates appear to be targeted by a direct interaction with the cyclin subunit, it seemed that PAP, with its multiple phosphorylation sites, would be a good candidate for such an association. To investigate this possibility, the ability of PAP to interact with a cyclin in vivo was tested. To this end, sf9 insect cells were co-infected with recombinant baculoviruses expressing bovine PAP I and human cyclin $B_1$. (PAP I and II arise from alternatively spliced mRNAs (36). They behave indistinguishably in their interaction with cdk/cyclins, and have been used interchangeably in the experiments described here.) Total cell extracts were prepared, subjected to immunoprecipitation with a rabbit polyclonal anti-PAP antibody, and the immunocomplex was analyzed by western blotting using a anti-cyclin $B_1$ monoclonal antibody (see Methods below). FIG. 1A, shows that cyclin B was present in the anti-PAP immunocomplex (lane 1), and that this was dependent on coexpression of PAP (lane 2). Lanes 3 and 4 show a western blot with anti-cyclin $B_1$ antibodies of the lysates prior to immunoprecipitation, which indicates that a significant fraction of the cyclin was associated with PAP.

Figure 1B:
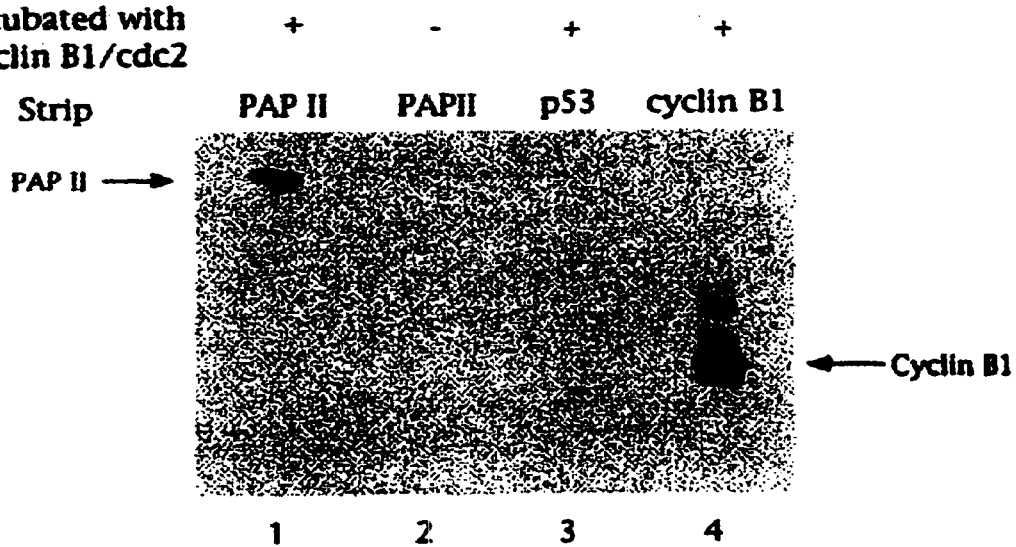

To characterize the PAP-cyclin $B_1$ interaction further, baculovirus-produced and purified histidine-tagged PAP II and human cyclin $B_1$/flu epitope-tagged p34cdc2 proteins were used in a modified far-western protein-protein interaction assay (FIG. 1B). Purified PAP II (1 µg) was immobilized on nitrocellulose by western blotting, renatured by serial dilution with guanidine-HCl, and strips were incubated with purified cyclin $B_1$/p34cdc2 (100 ng). After extensive washing (see Materials and Methods), the presence of cyclin $B_1$ bound to PAP II was determined by immunoreactivity to the anti-cyclin $B_1$ antibody (strip 1). The absence of cross-reactivity of PAP II with the anti-cyclin $B_1$ antibody was established by incubating a strip of PAP II under the above conditions except excluding incubation with cyclin $B_1$ (strip 2). A strip containing p53 instead of PAP was used to demonstrate the specificity of the interaction (strip 3). Strip 4 contained cyclin $B_1$. The results of this experiment indicate the existence of a direct interaction between PAP and cyclin $B_1$/p34cdc2.

Figure 2A:
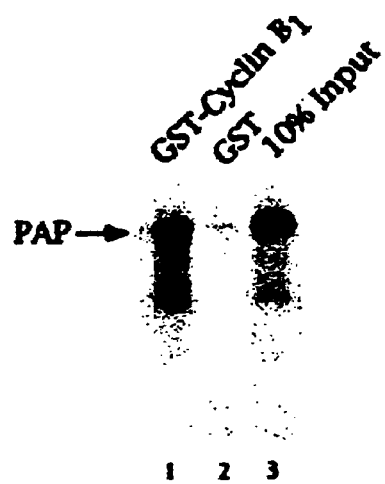

PAP Interacts With Cyclin $B_1$ Via Sequences N-terminal of the Serine/threonine-rich Regulatory Region To address the role of p34cdc2, if any, in the interaction of PAP with cyclin $B_1$, and to extend the above results to soluble proteins, a GST "pull-down" assay was employed. A GST-$B_1$ fusion protein was purified from recombinant baculovirus-infected sf9 cells, rebound to a glutathione-argarose matrix and incubated with in vitro translated $^{35}$S labeled PAP I. After extensive washing and elution, the elute was subjected to SDS-PAGE and the presence of PAP I was determined by autoradiography. In FIG. 2A, PAP I was detected in the eluate of the cyclin $B_1$ matrix (lane 1), but not in that of a GST control (lane 2), confirming the interaction of cyclin $B_1$ with PAP.

Figure 2B:
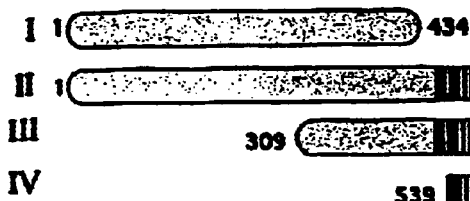
Figure 2C:
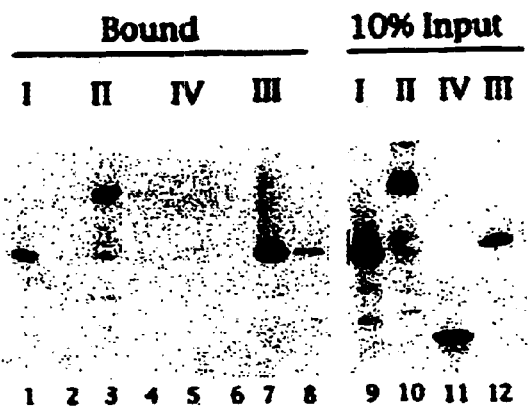

The same assay was next used to determine whether the Ser/Thr-rich C-terminus of PAP, which contains the seven known sites for cyclin $B_1$/p34cdc2 phosphorylation (10), also contains the residues responsible for associating with cyclin $B_1$. For this experiment, full-length in vitro translated ($^{35}$S-Met)-PAP I was again incubated with GST-cyclin $B_1$ bound to glutathione agarose beads, but this time along side of both N-terminal and C-terminal truncated PAP's (FIG. 2B). Both the wild type and N-terminal truncated species contain the Ser/Thr-rich region, the last comprising only this region (species II, III, and IV in panel B), but the C-terminal truncated PAP (species I in panel B) contains only residues N-terminal of the regulatory region. As seen in FIG. 2C, lanes 1, 3, 5 and 7, only those species with residues N-terminal of the regulatory region retained the ability to bind cyclin $B_1$, proving the Ser/Thr-rich region is neither necessary nor sufficient for PAP's association with cyclin $B_1$, whereas sequences N-terminal to this region, between residues 309 and 434, are.

PAP Contains a Novel Cyclin Recognition Motif

Inspection of the PAP sequence revealed that it contains a stretch of conserved amino acids with similarity to the consensus CRM, situated just N-terminal of the Ser/Thr-rich regulatory region (FIG. 3, also noted in FIG. 2B). Although other CRM-containing cdk substrates analyzed to date do not appear to interact with cyclin $B_1$, B-type cyclins do contain the residues in other cyclins necessary to contact the CRM (17, 37). The interaction between PAP and GST-cyclin $B_1$ is also resistant to high salt, which could suggest a hydrophobic association, another trait of a CRM-mediated interaction (37).

Figure 4A:
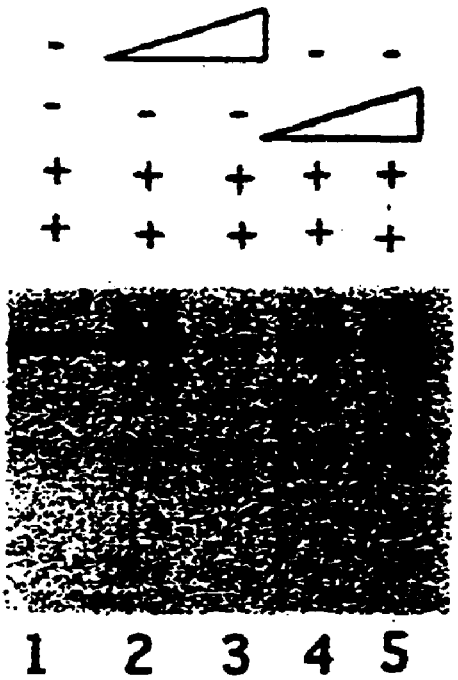

To test the functional significance of the putative PAP CRM, a series of experiments was carried out using a synthetic peptide (SEQ ID NO:1) spanning these eight residues of PAP (FIG. 3). These experiments were based on studies of the p21 family of cdk-inhibitors, and of cdk-substrates, including the transcription factor E2F-1, the retinoblastoma protein (pRB), and the related protein p107 (16, 17). As phosphorylation of pRB by cyclin A/cdk2, cyclin E/cdk2, and cyclin $D_1$/cdk4 can be inhibited by addition of increasing amounts of CRM-containing peptides (from p21, E2F-1, or pRB) to in vitro kinase assays, it was tested whether PAP's potential CRM-containing peptide could also inhibit pRB phosphorylation. Baculovirus-produced and purified flu-tagged pRB and human cyclin A/flu-tagged cdk2 were incubated under kinase conditions in the presence of $\gamma$-$^{32}$P adenosine 5'-triphosphate and analyzed by SDS-PAGE and subsequent autoradiography. As seen in FIG. 4A, PAP's CRM effectively inhibited pRB phosphorylation by cyclin A/cdk2 (lanes 2 and 3). The fact that pRB but not cyclin A phosphorylation (which appears to be a CRM-independent substrate; (37) was inhibited in the same reaction mixture provided an internal control for the specificity of the inhibition. In order to address the sequence specificity of this effect, a peptide with PAP's CRM scrambled was also tested, and it showed no effect on pRB phosphorylation (lanes 4 and 5). Similar results were obtained with cyclin E/cdk2 (data not shown). These results suggest that eight residues of PAP can act as a CRM, functionally interacting with cyclins A and E.

Figure 4B:
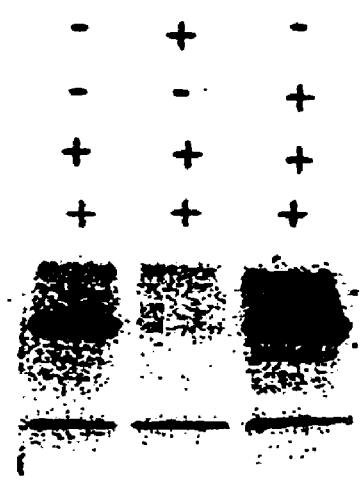

As shown above, PAP interacts directly with cyclin $B_1$. Therefore the ability of PAP's CRM to interact functionally with cyclin $B_1$ was tested by examining the effects of the 8-mer PAP peptide in the pRB phosphorylation assay. Strikingly, given the inactivity of other CRMs on cyclin $B_1$/cdc2 phosphorylation (17), PAP's CRM also strongly and specifically inhibited phosphorylation of pRB by cyclin $B_1$/cdc2 (FIG. 4B, compare lanes 1 and 3 with lane 2). As observed above with cyclin A, cyclin $B_1$ autophosphorylation was not affected. Together these results show that PAP contains a novel CRM-like sequence capable of functionally interacting with both $G_1$ and $G_2$ cyclins.

PAP Interacts With and is Phosphorylated by Cyclin A/cdk2

Figure 5B:
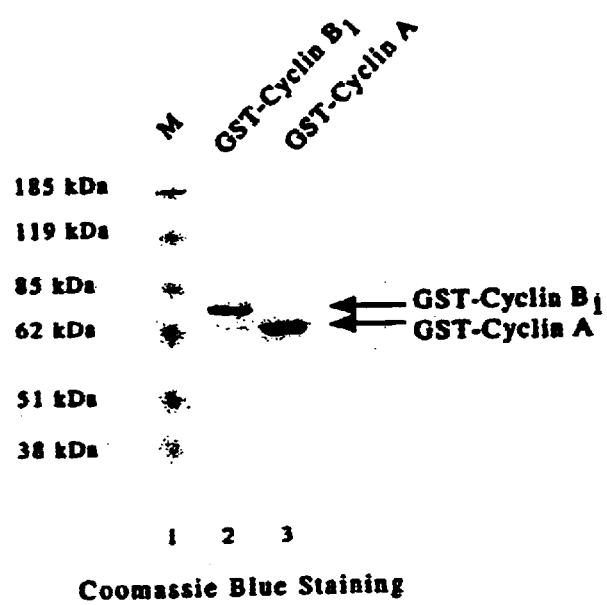

In order to determine whether the inhibition of cyclin A/cdk2 phosphorylation by the PAP peptide reflected an interaction between cyclin A and PAP, the ability of full-length PAP to bind cyclin A was investigated. To this end, a GST binding assay similar to that used in FIG. 2 was employed. In vitro translated $^{35}$S-Met-labeled PAP I was incubated with glutathione-agarose beads containing GST-cyclin $B_1$, GST-cyclin A or GST alone. As seen on the autoradiogram depicted in FIG. 5A, similar amounts of PAP I were present in the eluates of both cyclin $B_1$ (lane 1) and cyclin A (lane 2) matrices, but not in that of the GST control (lane 3), providing evidence for an interaction between cyclin A and PAP. (FIG. 5B shows a Coomassie blue-stained gel of the purified GST-cyclin fusion proteins used.)

Figure 5C:
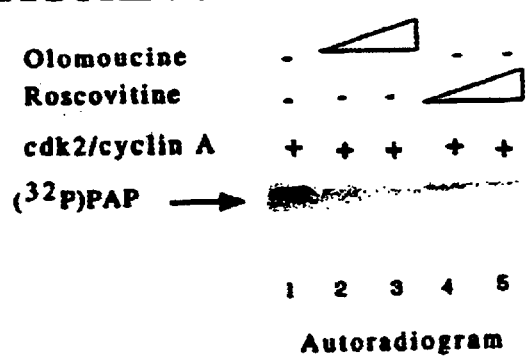

It was next tested whether PAP could bind cyclin A, as well as serve as a substrate for cyclin A/cdk2 phosphorylation. Phosphorylation was examined in an in vitro kinase assay using baculovirus-produced and purified human cyclin A/flu-tagged cdk2 and bacterial-produced and purified his-tagged PAP I. After incubation under kinase conditions in the presence of $\gamma$-$^{32}$P ATP, the reaction mixture was analyzed by SDS-PAGE and subsequent autoradiography. As seen in FIG. 5C, lane 1, $^{32}$P was efficiently incorporated into PAP. The specificity of cdk phosphorylation was controlled for by the addition of two specific cdk inhibitors, olomoucine and roscovitine, into the kinase reactions. As seen in lanes 2–5, incorporation of $^{32}$P into PAP was inhibited by both compounds. Taken together these results disclose that PAP can both bind cyclin A and serve as a substrate for phosphorylation by cyclin A/cdk2. This is consistent with the fact that PAP is phosphorylated throughout the cell cycle, not only in M-phase (7).

Novel, Concentration-dependent Effects of the 8-Mer Peptide (SEQ ID NO:1)

The above data show that PAP can interact with both cyclin A and cyclin $B_1$ and that at least in the case of cyclin $B_1$ this interaction is dependent on residues N-terminal of the Ser/Thr-rich PAP regulatory region, which encompass the PAP CRM. Next the CRM-dependence of PAP's interactions with cdk was examined with a series of binding and kinase assays using PAP as a substrate.

Figure 6A:
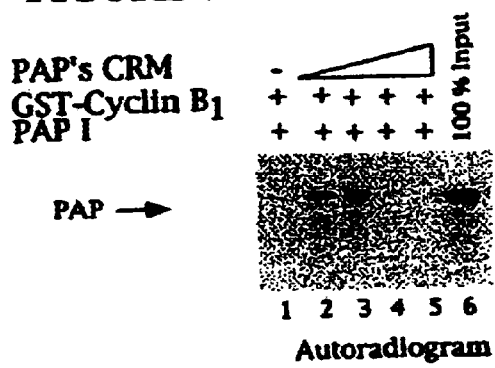
Figure 6B:
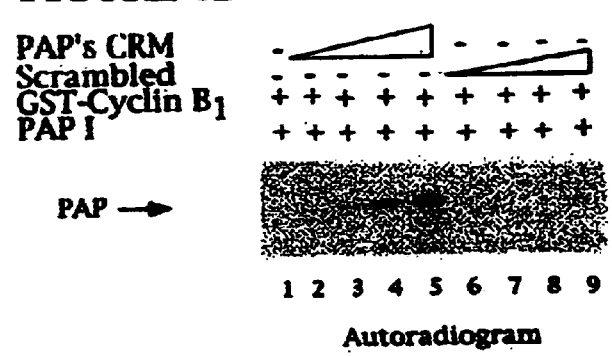

FIG. 6A and B show autoradiograms of GST "pull-down" assays using GST-cyclin $B_1$ and in vitro translated $^{35}$S-labeled PAP I. These experiments were carried out in the same way as those depicted in FIGS. 2 and 5, except that increasing amounts of the PAP CRM 8-mer (SEQ ID NO:1) were added to the glutathione-GST-cyclin $B_1$ matrix prior to PAP I (see Materials and Methods). Binding studies examining other CRM-dependent interactions with cyclins have demonstrated that addition of increasing amounts of CRM-containing peptides disrupt binding of the CRM-containing protein and the cyclin (e.g., 16, 17). The present experiments with the 8-mer (SEQ ID NO:1) also illustrate a disruption of the interaction between PAP and cyclin $B_1$ (at 40 and 70 $\mu$M peptide concentration; compare lanes 4 and 5 with lanes 2 and 3 of FIG. 6A). Unexpectedly, however, at lower concentrations of peptide (9 and 18 $\mu$M), a dramatic stimulation of binding was observed. Lanes 2 and 3, compared to lane 1, illustrate the striking enhancement of PAP I's binding to cyclin $B_1$, up to 50–100% bound at the lower concentrations of peptide (compare to lane 6, which displays 100% of the amount of PAP I used for each reaction). FIG. 6B illustrates more thoroughly the dose-dependent enhancement of PAP I-GST-cyclin $B_1$ binding by the CRM (2, 5, 10 and 20 $\mu$M; compare lane 1 with lanes 2–5). As a control for sequence specificity, an 8-mer peptide of scrambled CRM sequence (SEQ ID NO:4) was used (lanes 6–9). (Note that these experiments were done with a low concentration of GST-cyclin $B_1$, which does not allow significant PAP-cyclin $B_1$ interaction without addition of the lower concentrations the 8-mer (SEQ ID NO:1) (FIG. 6A, B and C, lane 1).) These results together suggest a unique, CRM-dependent interaction of PAP with cyclin $B_1$.

Figure 6C:
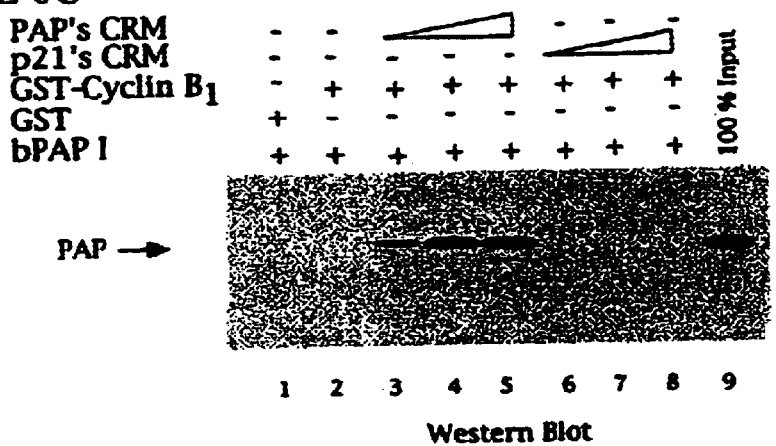
Figure 6D:
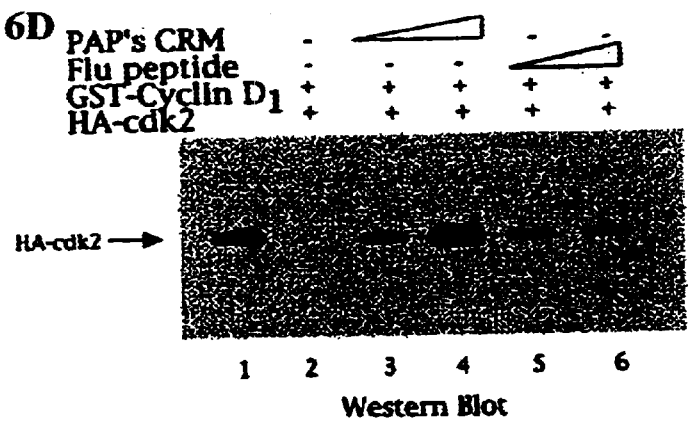

To determine whether the CRM-mediated enhancement of the PAP-cyclin association reflects a direct interaction between these two molecules, sources of PAP I were changed. Bacterial produced, purified his-PAP I (100 ng) was incubated with the GST-cyclin $B_1$ (1 μg) glutathione matrix, in the presence of the lower concentrations of the 8-mer (SEQ ID NO:1) that stimulated binding in FIG. 6A. After extensive washing and elution, the eluate was subjected to SDS-PAGE and Western blotting with an anti-PAP polyclonal antibody. As seen in FIG. 6C, lanes 3–5, compared to lane 2, addition of the peptide strongly stimulated the association of PAP with cyclin $B_1$ (2, 10 and 20 μM). Again, nearly 100% of the input PAP bound GST-cyclin $B_1$ at the highest concentration. As a control for specificity, an 8-mer peptide spanning the CRM of p21 (SEQ ID NO:5) was used. This peptide was chosen because it has been previously reported not to functionally associate with cyclin $B_1$ (2). As seen in lanes 6–8, p21's CRM had no effect on PAP-cyclin $B_1$ binding. (The apparent absence of PAP in lane 2 is due to the exposure time of the blot, designed to highlight the dose-dependent stimulation of PAP-cyclin binding by the peptide.) Together, these results support a mechanism by which the CRM peptide directly stimulates the PAP-cyclin $B_1$ interaction at low peptide concentrations, but subsequently inhibits the interaction at higher peptide concentrations. (Note that the abrupt switch from stimulation to inhibition (e.g., FIG. 6A, lanes 3 and 4) is highly reproducible.)

Although there have been no previous reports suggesting that a CRM peptide could enhance cyclin-substrate interactions, Adams et al. (17) reported that CRM peptides from p21 or E2F increased cyclin-cdk association. To determine if the 8-mer (SEQ ID NO:1) could also increase cyclin-cdk association a binding assay with GST-cyclin $D_1$ and baculovirus-produced and purified human flu-tagged cdk2 was used. Cyclin $D_1$'s binding to cdk2 was assayed for because of its documented weak affinity (38). Binding reactions were performed as above, and the eluates were analyzed for the presence of cdk2 by SDS-PAGE and subsequent Western blotting using an anti-flu antibody. As shown in FIG. 6C, the prior addition of the 8-mer (SEQ ID NO:1) (9 μM and 20 μM) into the binding reaction significantly increased the presence of cdk2 in the eluate (compare lanes 2–4), while addition of a control peptide was without significant effect (lanes 5 and 6). These results establish another similarity between the 8-mer (SEQ ID NO:1) and other characterized CRMs, namely the ability to stimulate the association of a cyclin and cdk.

The 8-Mer Peptide (SEQ ID NO:1) Stimulates S-phase in Resting Human Cells

In order to study the 8-mer (SEQ ID NO:1) ability to regulate cdk activity in vivo, the 8-mer peptide (SEQ ID NO:1), spanning PAP's CRM, was fused to residues derived from the *Drosophila antennapedia* homeodomain protein (penetratin, SEQ ID NO:2) thereby directing their efficient uptake across cell membranes (28, 29, 30, 31, 32). This combination of SEQ ID NO:1 and #2 is designated SEQ ID NO:3. As controls, a scrambled sequence (SEQ ID NO:4) was fused to the penetratin sequence and in a separate experiment the CRM of p21 (SEQ ID NO:5) (a cdk inhibitor) was fused to the penetratin.

Panel B of FIG. 7 is a graphical representation of DNA content of cells, derived from propidium iodide staining and subsequent the fluorescence-activated cell sorter (FACS) analysis. In this experiment, an immortalized human karitinocyte cell line (HaTCat) was treated with the cell-membrane permeable form of PAP's CRM (SEQ ID NO:3). SEQ ID NO:3 causes a dramatic increase in the S-phase population of cells. This is not observed with the scrambled sequence (SEQ ID NO:4), nor the p21 (SEQ ID NO:5) nor the penetratin sequence alone (SEQ ID NO:2).

The Membrane Permeable Version of the 8-Mer (SEQ ID NO:3) Kills Dividing Cells, but Protects Non-dividing Cells The cells used in FIG. 7B were confluent cells, as seen in the low percentage of cells in S-phase in the untreated population. The next results show how growing cells are affected by the membrane permeable version of the 8-mer (SEQ ID NO:3).

FIG. 8 is a graphical representation of the fold induction, over untreated control cells, of sub-G1 DNA content and S-phase DNA content of four different populations of HaTCat cells. These populations vary in their proliferation rates due to their confluency, starting with the least confluent population of cells, with 30% in S-phase, to the most confluent population, with only 3.5% in S-phase. Cycling cells, with over 30% of cells in S-phase, die when treated with the SEQ ID NO:3.

This death response is dramatically reduced the more confluent the cells become, as depicted in the graph in FIG. 8. As seen in the last group of cells, where the stimulation of S-phase is so high, cell death is in fact inhibited upon treatment with SEQ ID NO:3. Thus peptide protects the non-dividing cells.

Figure 8B:
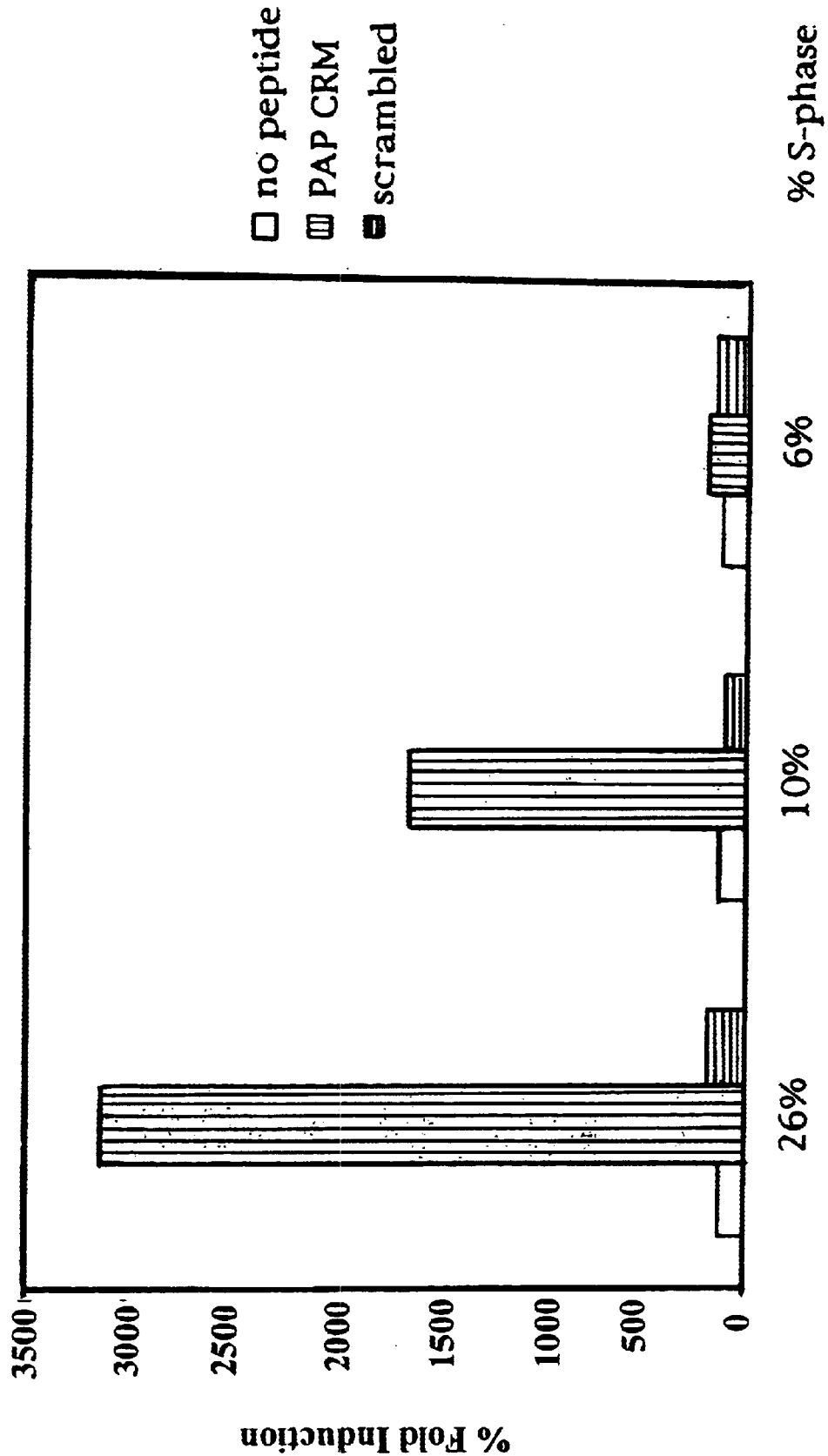

The response of Wi38, another immortalized human cell line, is shown in FIG. 8B. As with HaTCats, PAP's CRM is able to induce Wi38 death in a growth dependent manner. As cells become more confluent, a decrease in the percentage of cells in S-phase is seen, and is indicated below the bar graph. With the increase in confluency and the decease in growth, comes the 30 fold decrease in fold induction of sub G1 DNA content.

A molecular link of these two effects could be the retinoblastoma gene product, pRB. pRB has a well characterized anti-apoptotic affect in cells, most likely due to its ability to sequester E2F's pro-apoptotic activity (33). It is possible to explain the data described in FIG. 8 with the following model, presented in FIG. 9 and tested below. pRB's anti-apoptotic activity would be fully active in resting cells, where pRB is hypophosphorylated, allowing for the inhibition of death and the stimulation of proliferation upon treatment with SEQ ID NO:3. In growing, cycling cells, a large majority of pRB, and it s anti-apoptotic activity, would be inactivated by hyperphosphorylation (33, 34, 35), allowing for only cell death. In order to test this model, both wild type and pRB knock out mouse embryo fibroblasts (MEFs) were utilized in experiments.

The Membrane Permeable Version of the 8-Mer Peptide (SEQ ID NO:3) Stimulates Both Death and Cell Cycle Progression in Growing MEFs The data in FIG. 10 illustrate the same dual effects of PAP's CRM in MEFs, as seen in HaTCats. Panel A depicts the MEF's response to a concentration curve of SEQ ID NO:3. Sub-confluent cells were treated with the varying concentrations of SEQ ID NO:3 (1.87, 3.75, 7.5, 15, and 30 μM), as well as p21's CRM (SEQ ID NO:5)(30 μM) and the scrambled sequence (#4) (30 μM). After a one hour incubation, cells were harvested for propidium iodine staining and subsequent FACS analysis. The percentage of cells with sub-G1 DNA content and with S-phase DNA content dramatically increased in a SEQ ID NO:3 dose-dependent manner. No effects were seen with either p21's CRM or the scrambled sequence.

To further study the MEF's reactions to the membrane permeable peptide, SEQ ID NO:3, and to determine if the increase in S-phase depicts a stimulation or inhibition of proliferation, treatment with one concentration was followed at varying time points. Sub-confluent MEFs were treated with 30 μM SEQ ID NO:3, harvested at different time points, and their DNA content was analyzed by propidium iodide staining and subsequent FACS analysis. FIG. 10 panel B depicts the percentage of death initiated over time, as measured by sub-G1 DNA content. 30% of the cells die after the first hour of treatment, 50% by the forth. Panel B, depicts the cell cycle analysis over time of those cells that are not dying. Here, the stimulation of the cell cycle over time by SEQ ID NO:3, is clearly seen, ruling out an inhibitory effect. In the first hour, 25% of the cycling cells are induced into S-phase, and in time, into G2/M and back into G1.

The SEQ ID NO:3 Peptide Stimulates Only Death in pRB Knock Out MEFs

The ability of SEQ ID NO:3 to stimulate both death and proliferation in mouse embryo fibroblasts, allows us to test the model, wherein pRB inhibits cell death after treatment with SEQ ID NO:3, thereby allowing for stimulation of proliferation (FIG. 9). In the absence of pRB, cells would no longer have the anti-apoptotic activity of pRB, and treatment with SEQ ID NO:3 would lead only to cell death. In the experiment shown in FIG. 11, two genetically identical populations of cells were used, except that one was pRB minus, by way of knock out technology. The fold inductions of both sub-G1 and S-phase are represented in FIG. 11. Upon treatment with SEQ ID NO:3, here done in duplicate, the cells with pRB show at least a two-fold induction of S-phase after one hour of treatment. The cells without pRB show none, but therefore a dramatic (up to 50 fold) induction of death. These data provide evidence to support the model, that the retinoblastoma gene product, pRB, protects cells from death after treatment with SEQ ID NO:3, allowing for stimulation of proliferation.

The present application discloses a cyclin recognition motif in poly(A) polymerase (PAP) that controls PAP interaction with both G1 and G2 type cyclins. PAP cdk-phosphorylation is dependent on this interaction with cyclins, and it is disclosed that a low concentration of an 8-mer peptide (SEQ ID NO:1) spanning the core residues of PAP's CRM stimulates PAP-cyclin binding and, more significantly, inhibition of pRB phosphorylation by cdks.

The application shows the PAP CRM (the 8-mer peptide, SEQ ID NO:1) can regulate cdk activity in vivo. When introduced into cells as a membrane permeable peptide (SEQ ID NO:3), the peptide has dramatic affects on the life cycle of the cell. Human and murine cells show growth dependent responses to treatment with a cell-permeable form of the peptide. Dividing cells are killed while non-dividing cells are not. Evidence is also provided that pRB can regulate the cellular response to PAP's CRM and that where active pRB is not expressed (e.g. as in many neoplasias) the peptide is even more effective at killing dividing cells.

MATERIALS AND METHODS

Coimmunoprecipitation

Sf9 insect cells were infected with 1 pfu/cell of PAP-expressing and/or 3 pfu of cyclin $B_1$-expressing recombinant baculoviruses. After 40 hrs at 27° C., cells were harvested and lysed in 50 mM Tris, pH 8.0, 150 mM NaCl, 0.1% aprotinin, 10 mM benzamidine, 30 μg/ml leupeptin, 1 mg/ml bacitracin, 10 mg/ml α-2-macroglobulin and 0.35 mM phenylmethylsulfonyl fluoride (PMSF) for 15 minutes on ice. Lysates were spun at 37,000 g for 15 minutes at 4° C., and supernatants were collected. Protein G-sepharose beads (Pharmacia), anti-PAP polyclonal antisera, and supernatants were rocked for 3 hours at 4° C. After extensive washing with 50 mM Tris, pH 7.2, 200 mM NaCl, and 0.1% NP40, samples were subjected to 10% SDS-PAGE and Western blot analysis. Filters were probed with a monoclonal cyclin $B_1$ antibody (Santa Cruz).

Far Western Assays

The modified Far Western assay was carried out as previously described (39). One microgram of protein was used for each strip. After renaturation and blocking, 100 ng of purified cyclin $B_1$/cdc2 was incubated with the strips for 12 hours at 4° C. After extensive washing, strips were probed with the anti-cyclin $B_1$ monoclonal antibody.

GST Binding Assays

GST-Cyclin fusion proteins were expressed in recombinant baculovirus-infected cells. Infection and lysis were carried out as described (7). GST was expressed in *Escherichia coli* (JM 101), induced with 1 mM isopropyl-β-D-thiogalactopyranoside (IPTG) at 37° C. for 3 hours. Proteins were affinity purified using glutathione-Sepharose beads (Amersham Pharmacia Biotech AB). After extensive washing with NETN (20 mM Tris, pH 8.0, 100 mM NaCl, 0.5% NP40, 1 mM EDTA), proteins were eluted with 120 mM reduced glutathione (Sigma) and dialysed against 10 mM Hepes, pH 7.5, 5 mM NaCl, 0.1 mM EDTA, 1 mM DTT, 25% glycerol. Two microgram of each GST protein was rebound to glutathione-Sepharose beads. Unbound proteins were washed away and in vitro translated $^{35}$S-labeled PAPs (2 μls), purified bacterial PAP (100 ng), or purified HA-cdk2 (100 ng) were incubated with beads for 2 hrs at 24° C. in a total volume of 40 μl. For assays with peptides, 45 ng of purified GST-$B_1$ bound to glutathione-Sepharose beads, varying amounts of peptides, and 1 μl of in vitro translated $^{35}$S-labeled PAP were incubated for 2 hours at 24° C. in a total volume of 200 μl. In vitro translated proteins were produced using TNT rabbit reticulocyte lysate (Promega). Bovine PAP I (species II in FIG. 2B) was produced from bovine PAP I cDNA subcloned into a pET-14b plasmid containing a T7 promoter. The C-terminal truncated PAP (1-434) was in vitro transcribed/translated with the above-mentioned PAP I-pET-14b plasmid linearized with Dra III. One N-terminal truncated PAP (309-689aa) was produced from a template constructed by blunt-end ligation of PAP I-pET-14b, cut with Kpn I and Nco I. The second, N-terminal truncated PAP (539-689aa) was also produced from a template constructed by blunt-end ligation of PAP I-pET-14b, but cut with Spe I and Nde I.

Protein Phosphorylation

Two hundred nanogram of purified pRB, PAP or Histone H1 were incubated with 80 ng of purified cdks for 20 minutes at 30° C. in kinase buffer (25 mM HEPES, pH 7.5, 5 mM $MgCl_2$, 100 mM ATP, 0.5 μCi γ-$^{32}$P ATP, 0.1 mM DTT) in a total volume of 30 μl. Olomoucine (Calbiochem) and roscovitine (Calbiochem) were added where indicated at the concentrations shown in the figure legends. Where indicated, peptides were added at the concentrations shown. Peptides were added to reaction mixtures prior to substrates.

FACS Analysis

After treatment with or without cell membrane permeable peptides (Synpep), cells were trypsinized, centrifuged and washed in PBS. Cell were than fixed with methanol and kept at −20° C. for 40 min or overnight. After washing and equilibration in PBS, the cell pellet was resuspended in 1 ml of staining solution containing 50 μg of RNase A and 0.5 μg of propidium iodide per ml in PBS, and kept at room temperature for over 30 minutes. The cells were then applied to the fluorescence-activated cell sorter (FACSCalibur; Becton Dickson). The FACSCalibur program was used to sort and count the cells, and the Modfit program was used to calculate the percentage of cells in the $G_0/G_1$, S, and $G_2/M$ phases.

REFERENCES

1. Hunter, T., and J. Pines. 1994. Cyclins and cancer. II: Cyclin D and CDK inhibitors come of age. Cell 79:573–82.
2. Nigg, E. A. 1995. Cyclin-dependent protein kinases: key regulators of the eukaryotic cell cycle. Bioessays 17:471–80.
3. Barabino, S. M., and W. Keller. 1999. Last but not least: regulated poly(A) tail formation. Cell 99:9–11.
4. Wickens, M., P. Anderson, and R. J. Jackson. 1997. Life and death in the cytoplasm: messages from the 3' end. Curr Opin Genet Dev 7:220–32.
5. Foulkes, N. S., F. Schlotter, P. Pevet, and P. Sassone-Corsi. 1993. Pituitary hormone FSH directs the CREM functional switch during spermatogenesis. Nature 362:264–7.
6. Takagaki, Y., R. L. Seipelt, M. L. Peterson, and J. L. Manley. 1996. The polyadenylation factor CstF-64 regulates alternative processing of IgM heavy chain pre-mRNA during B cell differentiation. Cell 87:941–52.
7. Colgan, D. F., K. G. Murthy, C. Prives, and J. L. Manley. 1996. Cell-cycle related regulation of poly(A) polymerase by phosphorylation. Nature 384:282–5.
8. Ballantyne, S., A. Bilger, J. Astrom, A. Virtanen, and M. Wickens. 1995. Poly (A) polymerases in the nucleus and cytoplasm of frog oocytes: dynamic changes during oocyte maturation and early development. RNA 1:64–78.
9. Zhao, W., and J. L. Manley. 1998. Deregulation of poly(A) polymerase interferes with cell growth. Mol Cell Biol 18:5010–20.
10. Colgan, D. F., K. G. Murthy, W. Zhao, C. Prives, and J. L. Manley. 1998. Inhibition of poly(A) polymerase requires p34cdc2/cyclin B phosphorylation of multiple consensus and non-consensus sites. Embo J 17:1053–62.
11. Dynlacht, B. D., O. Flores, J. A. Lees, and E. Harlow. 1994. Differential regulation of E2F transactivation by cyclin/cdk2 complexes. Genes Dev 8:1772–86.
12. Horton, L. E., and D. J. Templeton. 1997. The cyclin box and C-terminus of cyclins A and E specify CDK activation and substrate specificity. Oncogene 14:491–8.
13. Kelly, B. L., K. G. Wolfe, and J. M. Roberts. 1998. Identification of a substrate-targeting domain in cyclin E necessary for phosphorylation of the retinoblastoma protein. Proc Natl Acad Sci USA 95:2535–40.
14. Pan, Z. Q., A. Amin, and J. Hurwitz. 1993. Characterization of the in vitro reconstituted cyclin A or B1-dependent cdk2 and cdc2 kinase activities. J Biol Chem 268:20443–51.
15. Peeper, D. S., L. L. Parker, M. E. Ewen, M. Toebes, F. L. Hall, M. Xu, A. Zantema, A. J. van der Eb, and H. Piwnica-Worms. 1993. A- and B-type cyclins differentially modulate substrate specificity of cyclin-cdk complexes. Embo J 12:1947–54.
16. Adams, P. D., X. Li, W. R. Sellers, K. B. Baker, X. Leng, J. W. Harper, Y. Taya, and W. G. Kaelin, Jr. 1999. Retinoblastoma protein contains a C-terminal motif that targets it for phosphorylation by cyclin-cdk complexes. Mol Cell Biol 19:1068–80.
17. Adams, P. D., W. R. Sellers, S. K. Sharma, A. D. Wu, C. M. Nalin, and W. G. Kaelin, Jr. 1996. Identification of a cyclin-cdk2 recognition motif present in substrates and p21-like cyclin-dependent kinase inhibitors. Mol Cell Biol 16:6623–33.
18. Chen, I. T., M. Akamatsu, M. L. Smith, F. D. Lung, D. Duba, P. P. Roller, A. J. Fornace, Jr., and P. M. O'Connor. 1996. Characterization of p21Cip1/Waf1 peptide domains required for cyclin E/Cdk2 and PCNA interaction. Oncogene 12:595–607.
19. Dynlacht, B. D., K. Moberg, J. A. Lees, E. Harlow, and L. Zhu. 1997. Specific regulation of E2F family members by cyclin-dependent kinases. Mol Cell Biol 17:3867–75.
20. Krek, W., M. E. Ewen, S. Shirodkar, Z. Arany, W. G. Kaelin, Jr., and D. M. Livingston. 1994. Negative regulation of the growth-promoting transcription factor E2F-1 by a stably bound cyclin A-dependent protein kinase. Cell 78:161–72.
21. Lin, J., C. Reichner, X. Wu, and A. J. Levine. 1996. Analysis of wild-type and mutant p21WAF-1 gene activities. Mol Cell Biol 16:1786–93.
22. Ma, T., N. Zou, B. Y. Lin, L. T. Chow, and J. W. Harper. 1999. Interaction between cyclin-dependent kinases and human papillomavirus replication-initiation protein E1 is required for efficient viral replication. Proc Natl Acad Sci USA 96:382–7.
23. Morris, M. C., and G. Divita. 1999. Characterization of the interactions between human cdc25C, cdks, cyclins and cdk-cyclin complexes. J Mol Biol 286:475–487.
24. Petersen, B. O., J. Lukas, S. r. CS, J. Bartek, and K. Helin. 1999. Phosphorylation of mammalian CDC6 by Cyclin A/CDK2 regulates its subcellular localization. Embo J 18:396–410.
25. Saha, P., Q. Eichbaum, E. D. Silberman, B. J. Mayer, and A. Dutta. 1997. p21CIP1 and Cdc25A: competition between an inhibitor and an activator of cyclin-dependent kinases. Mol Cell Biol 17:4338–45.
26. Zhu, L., E. Harlow, and B. D. Dynlacht. 1995. p107 uses a p21CIP1-related domain to bind cyclin/cdk2 and regulate interactions with E2F. Genes Dev 9:1740–52.
27. Bond, G. L., C. Prives, and J. L. Manley 2000. Poly(A) polymerase phosphorylation is dependent on novel interactions with cyclins Mol Cell Biol. 20:5310–20.
28. Ball, K. L., S. Lain, R. Fahraeus, C. Smythe, and D. P. Lane 1997. Cell-cycle arrest and inhibition of Cdk4 activity by small peptides based on the carboxy-terminal domain of p21WAF1 Curr Biol. 7:71–80.
29. Bonfanti, M., S. Taverna, M. Salmona, M. D'Incalci, and M. Broggini 1997. p21WAF1-derived peptides linked to an internalization peptide inhibit human cancer cell growth Cancer Res. 57:1442–6.
30. Chen, Y. N., S. K. Sharma, T. M. Ramsey, L. Jiang, M. S. Martin, K. Baker, P. D. Adams, K. W. Bair, and W. G. Kaelin, Jr. 1999. Selective killing of transformed cells by cyclin/cyclin-dependent kinase 2 antagonists [see comments] Proc Natl Acad Sci USA. 96:4325–9.
31. Fahraeus, R., S. Lain, K. L. Ball, and D. P. Lane 1998. Characterization of the cyclin-dependent kinase inhibitory domain of the INK4 family as a model for a synthetic tumour suppressor molecule Oncogene. 16:587–96.

32. Fahraeus, R., J. M. Paramio, K. L. Ball, S. Lain, and D. P. Lane 1996. Inhibition of pRb phosphorylation and cell-cycle progression by a 20-residue peptide derived from p16CDKN2/INK4A Curr Biol. 6:84–91.
33. Harbour, J. W., and D. C. Dean 2000. Rb function in cell-cycle regulation and apoptosis Nat Cell Biol. 2:E65–7.
34. Harbour, J. W., R. X. Luo, A. Dei Santi, A. A. Postigo, and D. C. Dean 1999. Cdk phosphorylation triggers sequential intramolecular interactions that progressively block Rb functions as cells move through G1 Cell. 98:859–69.
35. Hatakeyama, M., and R. A. Weinberg 1995. The role of RB in cell cycle control Prog Cell Cycle Res.1:9–19.
36. Zhao, W., and J. L. Manley. 1996. Complex alternative RNA processing generates an unexpected diversity of poly(A) polymerase isoforms. Mol Cell Biol 16:2378–86.
37. Schulman, B. A., D. L. Lindstrom, and E. Harlow. 1998. Substrate recruitment to cyclin-dependent kinase 2 by a multipurpose docking site on cyclin A. Proc Natl Acad Sci USA 95:10453–8.
38. LaBaer, J., M. D. Garrett, L. F. Stevenson, J. M. Slingerland, C. Sandhu, H. S. Chou, A. Fattaey, and E. Harlow. 1997. New functional activities for the p21 family of CDK inhibitors. Genes Dev 11:847–62.
39. Kohtz, J. D., S. F. Jamison, C. L. Will, P. Zuo, R. Luhrmann, M. A. Garcia-Blanco, and J. L. Manley. 1994. Protein-protein interactions and 5'-splice-site recognition in mammalian mRNA precursors. Nature 368:119–24.

What is claimed is:

1. A peptide consisting of consecutive amino acids having the sequence shown in SEQ ID NO:1.

2. A peptide consisting essentially of consecutive amino acids having the sequence shown in SEQ ID NO:3.

3. A composition comprising the peptide of claim 1 or 2 and a pharmaceutically acceptable carrier.

4. The composition of claim 3, wherein the peptide and the carrier are capable of passing through a cell membrane.

* * * * *